Figure 3:
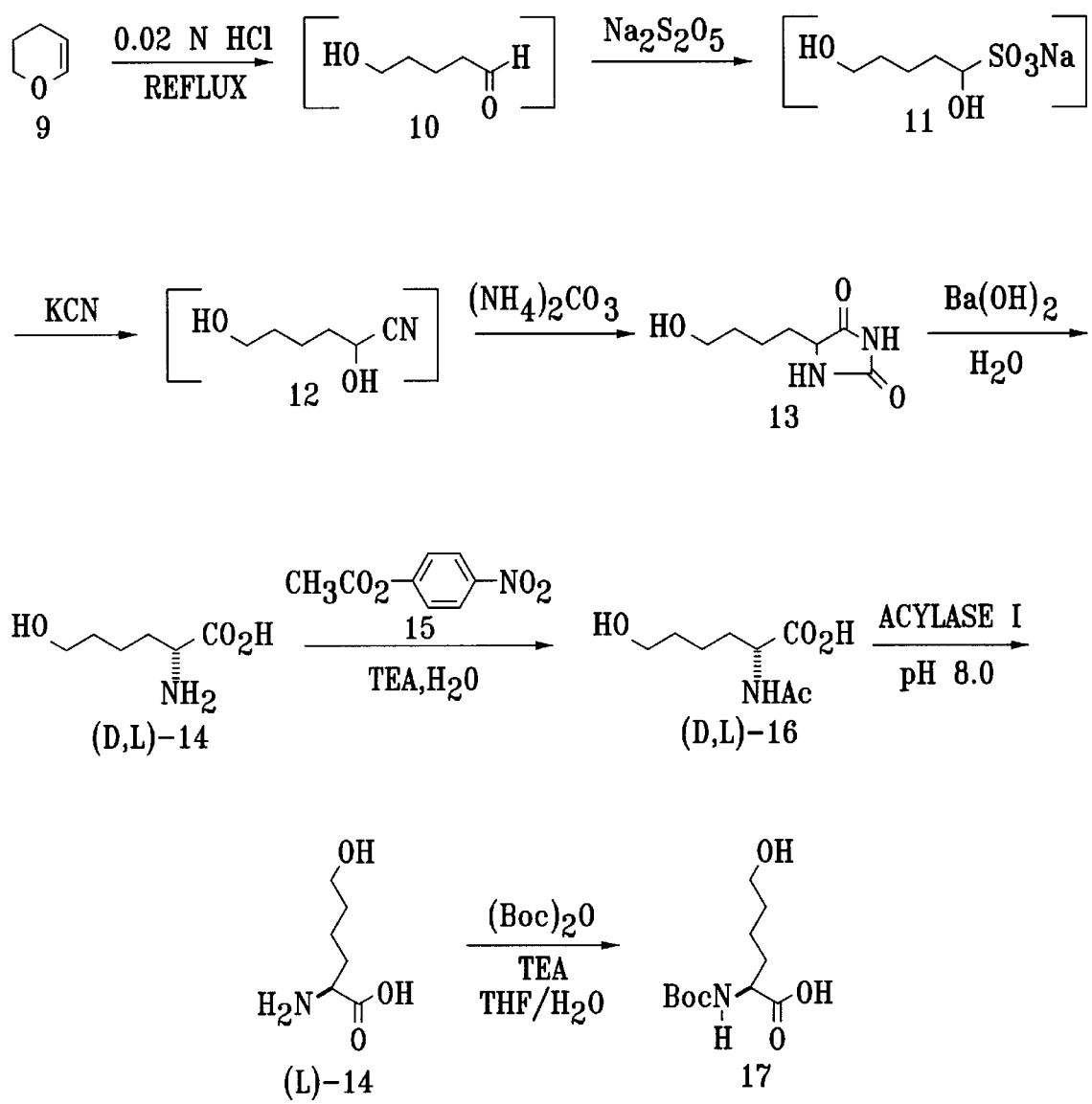

US006063919A

United States Patent [19]
Gaudioso et al.

[11] Patent Number: 6,063,919
[45] Date of Patent: May 16, 2000

[54] PROCESS FOR THE SYNTHESIS OF EXOCHELINS

[75] Inventors: Larry A. Gaudioso; Michael A. Weglarz, both of Salt Lake City, Utah

[73] Assignee: Keystone BioMedical, Inc., Los Angeles, Calif.

[21] Appl. No.: 09/134,084

[22] Filed: Aug. 14, 1998

[51] Int. Cl.[7] .............................................. C07D 223/10
[52] U.S. Cl. ......................................................... 540/524
[58] Field of Search ........................................... 540/524

[56] References Cited

U.S. PATENT DOCUMENTS

| | | | |
|---|---|---|---|
| 5,721,209 | 2/1998 | Horwitz et al. | 514/11 |
| 5,786,326 | 7/1998 | Horwitz | 514/11 |

OTHER PUBLICATIONS

Macham, L.P., Ratledge, C. and Nocton J.C., "Extracellular Iron Acquisition by Mycobacteria: Role of the Exochelins and Evidence Against the Participation of Mycobactin", *Infection and Immunity*, Dec. 1975, pp. 1242–1251, vol. 12, No. 6.

Barclay, R. and Ratledge, C., "Mycobactins and Exochelins of *Mycobacterium tuberculosis*, M. bovis, M. africanum and Other Related Species", *Journal of General Microbiology*, 1988, pp. 134, 771–776.

Machum, L.P. and Ratledge, C., *Journal of General Microbiology*, 1975, pp. 89, 379–382.

Mauer, P.J. and Miller, J.J. "Total Synthesis of a Mycobactin: Mycobatin S2", 1983, *J. Am. Chem. Soc.*, pp. 240–245, vol. 105.

Mauer, P.J. and Miller, M.J., "Microbial Iron Chelators: Total Synthesis of Aerobactin and Its Constituent Amino Acid, $N^6$–Acetyl–$N^6$–hydroxylysine" 1982, *J. Am. Chem. Soc.* 104, pp. 3096–3101.

Farkas, L. et al., "The Syntheses of Wightin and Echioidinn, Two Flavones From Andrographis Wightiana", 1967, *Tetrahedron*, vol. 23, pp. 741–744.

Schniepp, L.E. and Geller, H.H., "Preparation of Dihydropyran δ–Hydroxyvaleraldehyde and 1,5–Pentanediol from Tetrahydrofurfuryl Alcohol"1946, *J.An, Chem. Soc.*, vol. 68, pp. 1646–1648.

Gaudry, R., The Synthesis ofD, L–α–Amino–ε–Hydroxycaproic Acid and a New Synthesis of D,L–LYSINE[1], *Can. J. Res. Sec.B*, 1946, vol. 26, pp. 387–392.

Dreyfuss, P, "Synthesis and Some Pharmacological Properties of 8–ε–Hydroxynorleucine–Vasopressin", *J.Med. Chem.*, 1974, vol. 17(2), pp. 252–255.

Berlinguet, L. and Gaudry, R Enzymatic Resolution of DL–α–Amino–δ–Hydroxy–n–Valeric Acid, 1952, *J.Biol. Chem.*, vol. 198. pp. 765–769.

Bodanszky, M. et al., 1978 "Cholecystokinin (PNCREOZYMIN). 4.[1]Synthesis and Properties of a Biologically Active Analogue of the C–Terminal Heptapetptide with ε–Hydroxynorlecucine Sulfate Replacing Tyrosine Sulfate"*J.Med. Chem.* vol. 21(10), pp. 1030–1035.

Maurer, P.J. and Miller, M.J.1981, Mycobactins: Synthesis of (–)–Cobactin T from ε–Hydroxynorleucine, *J. Org. Chem. Soc* vol. 46(13), 2835–2836.

Birnbaum, S.M. Levintow, L. Kingsley, R.B. and Greenstein, J.P., "Specificity of Amino Acid Acylases"1952, *J.Biol. Chem,* , vol. 194, pp. 455–470.

Corey, E. J. and Vankateswarlu, A., "Protection of Hydroxyl Groups as tert–Butyldimethylsilyl Derivatives" 1972, *J.Am. Chem. Soc.*,vol. 94, pp. 6190–6191.

Sieber, P., "264.Der 2–Trimethylsilylathyl–Rest als selektiv abspaltbare Carboxy–Schutzgruppe[1])[2])", 1977, *Helv. Chim. Acta*, vol. 60, pp. 2711(b)–2716.

Gerlach, H., "298. 2–(Trimethylsilyl) athylester als Carboxylschutzgruppe; Anwendung bei der Synthese des (–)–(S)–Curvularins" 1977, *Helv. Chim. Acta*, Vol 60, pp. 3039–3044.

Mitsunobu, O., "The Use of Diethyl Azodicarboxylate and Triphenylphosphine in Synthesis and Transformation of Natural Products", 1981, *Synthesis*, 1981, pp. 1–28.

Hu, J. and Miller, M.J., "Total Synthesis of a Mycobactin a Siderophore and Growth Promoter of Mycobacterium Smegmatis, and Determination of its Growth Inhibitory Activity against *Mycobacterium tuberculosis*", 1997, pp. 3462–3468, *J. Chem. Soc.* 119.

Sieglinde Friedrich–Bochnitschek, Herbert Waldmann, and Horst Kunz, Allyl Esters as Carboxy Protecting Groups in the Synthesis of O–Glycopeptides[1], *J.Org. Chem*, 1989, vol. 54, pp. 751–756.

*Primary Examiner*—Mukund J. Shah
*Assistant Examiner*—Brenda Coleman
*Attorney, Agent, or Firm*—Michael J. Ram; Koppel & Jacobs

[57] ABSTRACT

A process for the synthesis of an Exochelin comprising the steps of generating L-N-[(2-benzyloxy-(benzoyl)] serine or L-N-[2-benzyloxy (benzoyl)] threonine, creating L-N-t-Boc-ε-hydroxynorleucine and reacting same to produce L-N-Boc-ε-bromonorleucine trimethylsilylethyl ester, providing a dicarboxylic acid and forming an O-benzyl methyl hydroxamate from the dicarboxylic acid, coupling the O-benzyl methyl hydroxamate with the L-N-Boc-ε-bromonorleucine trimethylsilylethyl ester to give an L-$N^2$-Boc-$N^6$-methyl,$N^6$-(benzyloxy) lysine 2-trimethylsilylethyl ester which incorporates the dicarboxylic acid as modified above, removing the N-tert-butoxycarbonyl protecting group from the L-$N^2$-Boc-$N^6$-methyl, $N^6$-(benzyloxy) lysine 2-trimethylsilylethyl ester to yield a substituted lysine, and coupling the same with the L-N-[2-benzyloxy (benzoyl) serine or -threonine to yield a 2-trimethyl silylethyl ester of dibenzyl Exochelic acid, transforming the 2-trimethyl silylethyl ester of dibenzyl Exochelic acid to dibenzyl Exochelic acid, preparing benzyl epi-cobactin, forming an ester bond between the dibenzyl Exochelic acid and benzyl epi-cobactin to form an intermediate, and, hydrogenolytically removing three benzyl groups from said intermediate, resulting in the synthesized Exochelin. More particularly, a synthesis for Exochelin 786SM (R) is disclosed wherein the dicarboxylic acid is suberic acid and the serine form is utilized.

12 Claims, 20 Drawing Sheets

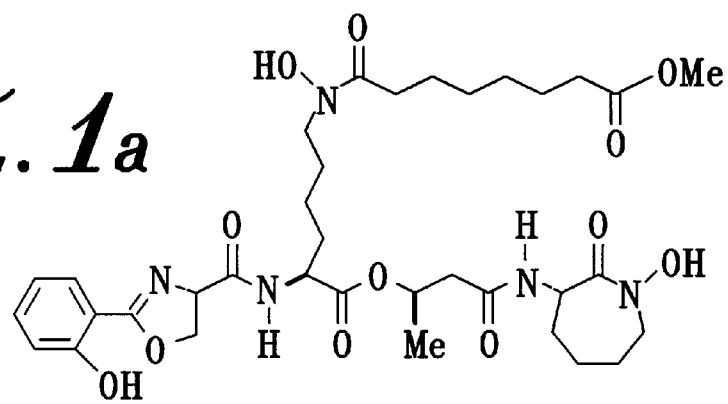
EXOCHELIN 786SM(R)
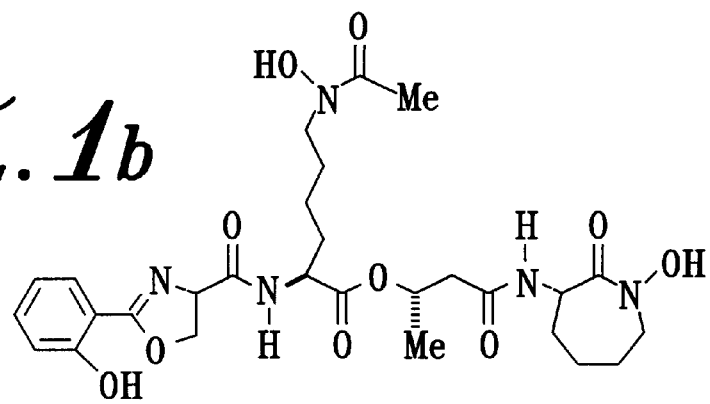
MYCOBACTIN S2
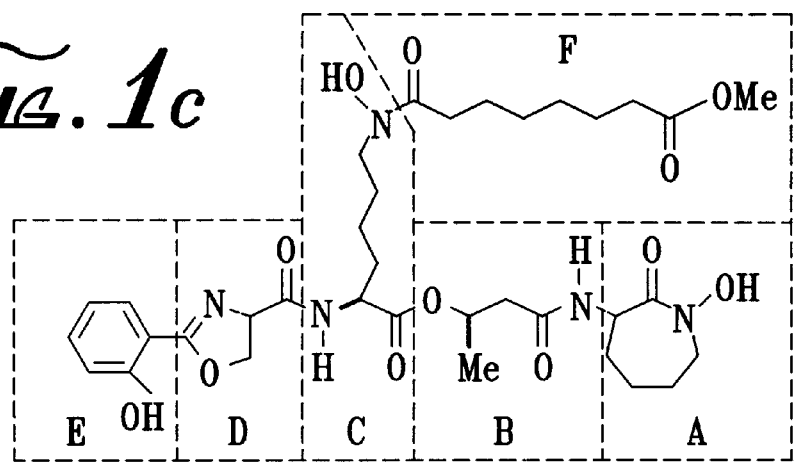

FIG. 2
SCHEME I
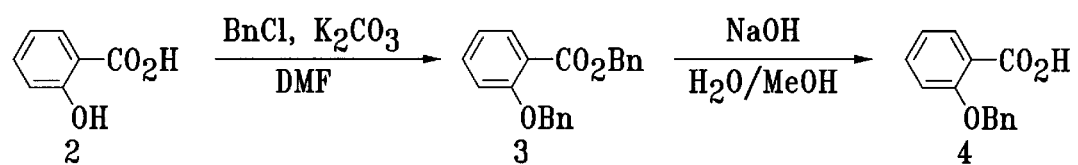
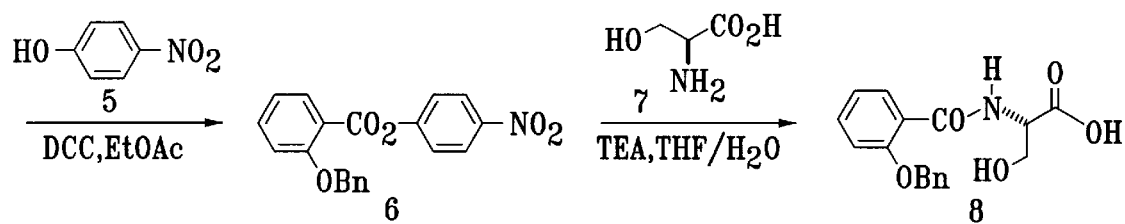
FIG. 4
SCHEME III
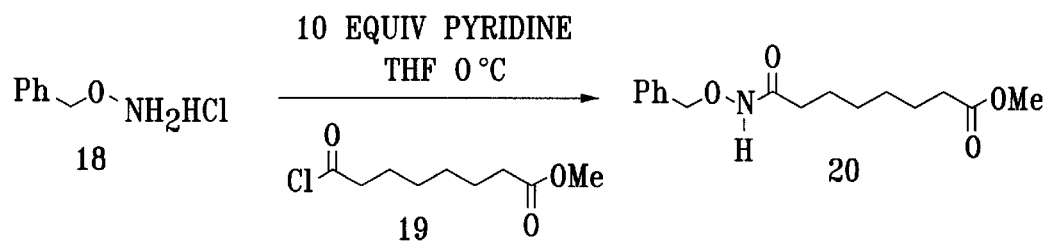

SCHEME II

SCHEME IV

SCHEME V

DIBENZYL EXOCHELIC ACID

SCHEME VI

BENZYL EPI-COBACTIN

SCHEME VII

EXOCHELIN 786SM(R)
$C_{35}H_{51}N_5O_{12}$ M.W. 733.82

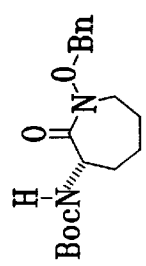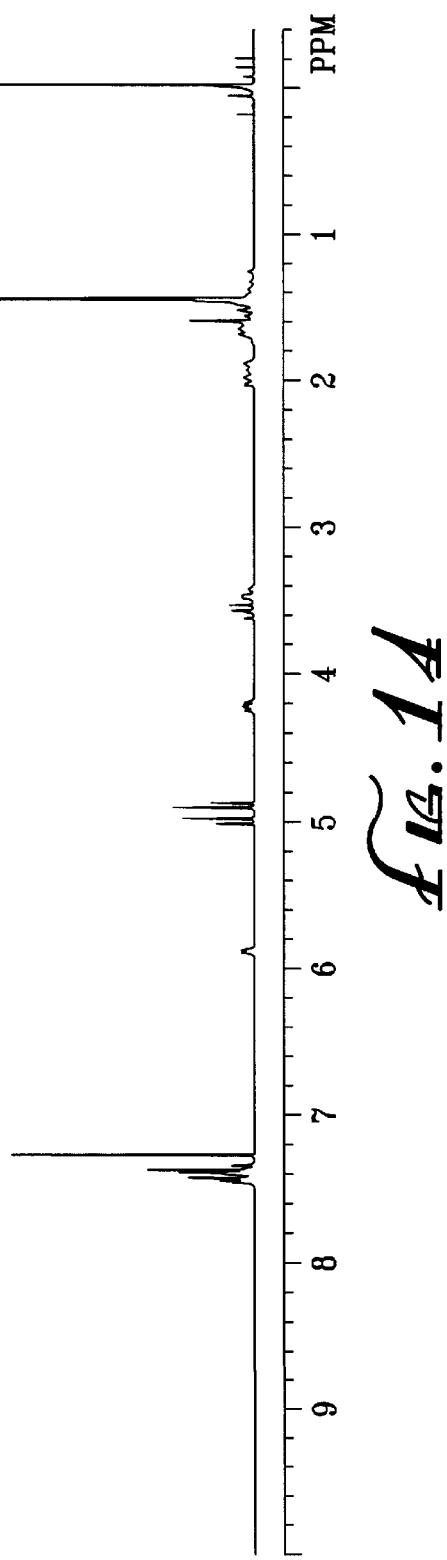
FIG. 14

Figure 18:
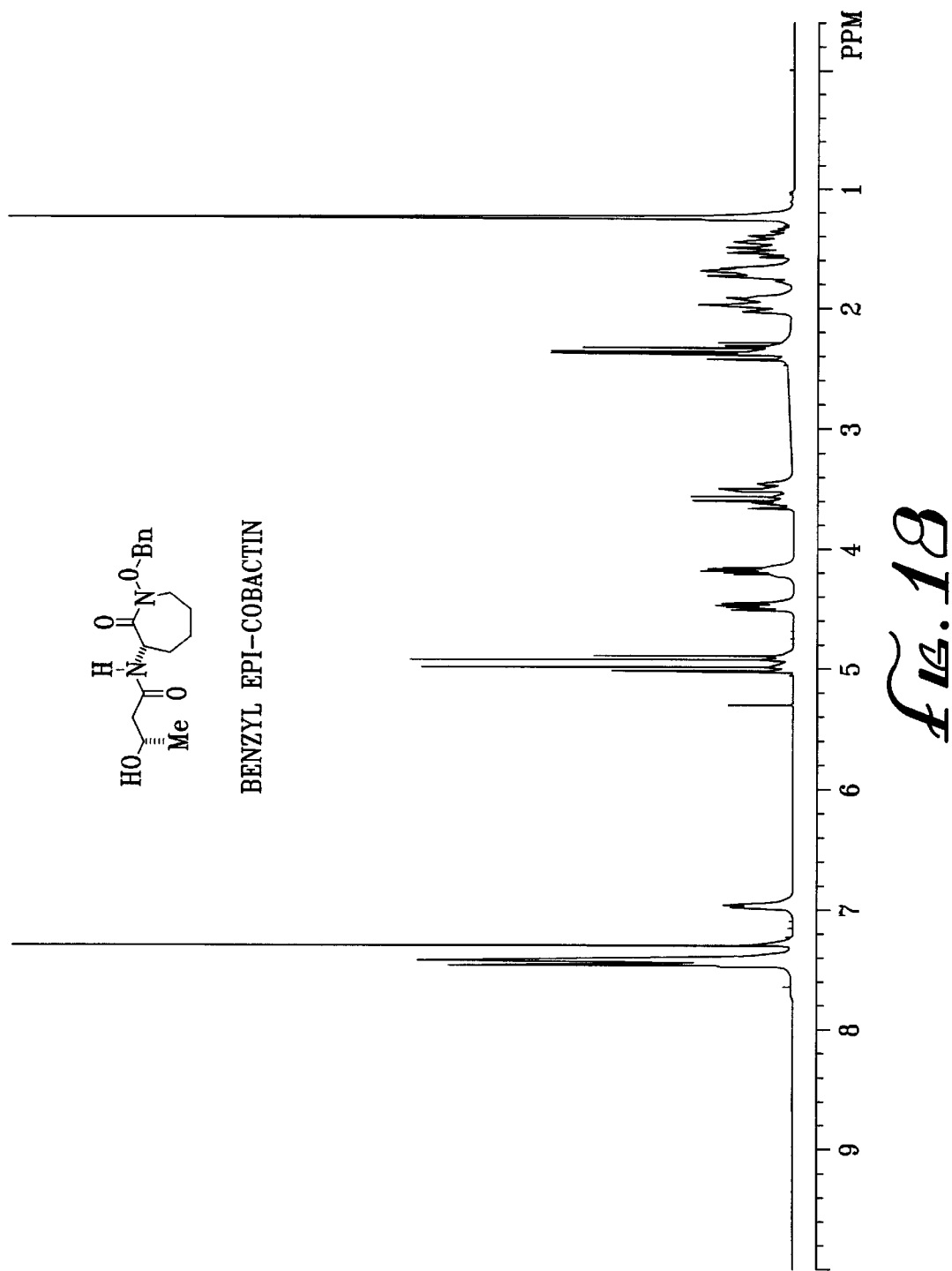

Fig. 18 BENZYL EPI-COBACTIN

PROCESS FOR THE SYNTHESIS OF EXOCHELINS

BACKGROUND OF THE INVENTION

The present application expressly incorporates by reference U.S. Ser. No. 08/383,180, now U.S. Pat. No. 5,721,209, U.S. Ser. No. 08/796,791, now U.S. Pat. No. 5,786,326, U.S. Ser. No. 08/882,122, now U.S. Pat. No. 5,837,677 and U.S. Ser. No. 08/960,714, now U.S. Pat. No. 5,994,346 each of which are subject to an exclusive license or assignment to a common entity, said entity being the assignee of this application. Said patents and applications all discuss medical applications of biologically prepared, purified Exochelins. Said Exochelins are prepared by synthetic pathways set forth and claimed herein.

The present invention relates to a heretofore undisclosed process for the synthetic generation of high affinity, iron binding compounds known as Exochelins, and more particularly, to a synthetic process for making Exochelins and to modifications to these newly synthesized compounds to vary their physiological properties, including applications of these newly synthesized and utile compounds for diagnosing and treating disease in mammals.

The above-referenced U.S. Patents and applications have shown that exochelins have unique physiological benefits. For example, in acute myocardial infarction, cardiac tissue is damaged by two sequential events, hypoxia in the ischemic phase and oxidative damage in the reperfusion phase. Myocardium damaged in the ischemic phase can be salvaged by reintroduction of blood into the ischemic area. However, reperfusion can result in injury to the reperfused tissue as a result of an inflammatory response caused by the migration of leucocytes into the tissue and the production of reactive oxygen species. One of the most reactive species is the hydroxyl radical (—OH) which is generated in the presence of iron, and which often results in cell death or related oxidative tissue damage.

Prevention of the formation of (—OH) prevents lethal cell damage by several mechanisms. It is well known that the formation of (—OH) is dependent on the presence of free iron, and that iron chelators will prevent reperfusion injury. For example, the iron chelator desferoxamine, when administered prior to reperfusion, prevents injury and reduces myocardial infarct size during coronary artery occlusion and reperfusion. However, reperfusion injury occurs rapidly after the reestablishment of blood flow to the ischemic myocardium.

The formation of the (—OH) radical is dependent on the presence of free iron and iron chelators can scavenge the free iron and thus render the iron unavailable to catalyze the hydroxyl radical formation. However, prior known chelating means either do not prevent (—OH) production by the Fenton Reaction (i.e., EDTA), or enter the cells too slowly (i.e., desferoxamine). As a result, sufficient quantities of the chelating agent are not available to act rapidly enough to chelate enough iron to prevent the formation of (—OH) and cell damage and destruction which results.

Desferoxamine has been demonstrated to be effective if administered prior to occurrence of the myocardial infarct but to be ineffective if administered at or after the onset of reperfusion. Similar injury to heart tissue can occur as a result of heart bypass procedures, such as during open heart surgery, or to other body organs when they are deprived of oxygenated blood as a result of surgery or injury. Thus, iron scavenging chelators are clearly needed to prevent oxidative tissue damage.

Prior to the disclosures of Horwitz, et al., compounds referred to as Exochelins had been briefly described, and their general finction in the growth of mycobacteria was likewise discussed by Macham, Ratledge and Barclay at the University of Hull in England (MACHAM, L. P., RATLEDGE, C. and NOCTON J. C., "Extracellular Iron Acquisition by Mycobacteria: Role of the Exochelins and Evidence Against the Participation of Mycobactin", *Infection and Immunity*, December 1975, pp.1242–1251, Vol. 12, No.6; BARCLAY, R. and RATLEDGE, C., "Mycobactins and Exochelins of *Mycobacterium tuberculosis, M. bovis, M. africanum* and Other Related Species", *Journal of General Microbiolog*, 1988, pp.134, 771–776; MACHAM, L. P. and RATLEDGE, C., *Journal of General Microbiology*, 1975, pp. 89, 379–382).

Macham identified the existence of a substance found in the extracellular fluid, which he referred to as 'Exochelin'. Macham further described the materials he referred to as Exochelins as water and chloroform soluble compounds having the ability to chelate free iron. Macham et al. did not isolate or purify the Exochelins, merely characterizing them as penta- or hexapeptide, with molecular weights in the range of 750 to 800, inter alia.

According to Macham's work, his compounds have similarities to mycobactin—which is located in the cell wall and functions to transmit iron to the interior of the cell. However, unlike mycobactin, a lipophilic, water insoluble molecule which is unable to diffuse into, and assimilate free iron from the extracellular environment, Exochelin functions at physiological pH to sequester iron from other iron bearing compounds in the serum. Also, depending on the bacterial source of the Exochelin, Macham et al. disclosed that the molecules may also include salicylic acid or beta-alanine.

Barclay et al. (Ibid.)likewise described the production of the Exochelins from twenty-two different strains of *M. tuburculosis* and related species. However, neither these, nor any other known prior investigators, determined the specific structure of Exochelins, or identified any application for the same outside of their function as a transport medium for iron to mycobactin located in the cell wall.

In sum, Macham et al. recognized that after sequestering iron from, for example, ferritin or transferrin (and the like iron bearing compounds found in the serum) the sequestered iron is presented in a form that can be transferred to mycobactin, while Barclay et al. described production of Exochelins from known mycobacterial strains without precisely elucidating their structure.

The total synthesis of a related compound, Mycobactin S2, was reported by Maurer and Miller in 1983 (MAUER, P. J. and MILLER, M. J. "Total Synthesis of a Mycobactin: Mycobactin S2", 1983, *J. Am. Chem. Soc.*, pp. 240–245, Vol. 105). Mauer et al. successfully prepared 29 milligrams of a Mycobactin utilizing a complex, multi-step synthetic pathway. Mycobactin S2, however, is significantly different from the target molecule according to the synthesis of the present invention. Likewise, Exochelin synthesis remains unreported to date.

The following references provide teachings relevant to the synthesis according to the present invention:

MAUER, P. J. and MILLER, M. J., 1982, *J. Am. Chem. Soc.*, 104, 3096;

FARKAS, L. et al., 1967, *Tetrahedron*, 23, 741;

SCHNIEPP, L. E. and GELLER, H. H., 1946, *J.Am. Chem. Soc.*, 68, 1646;

GAUDRY,R., 1948, *Can. J. Res. Sect. B*, 26, 387;

DREYFUSS, P., 1974. *J. Med. Chem.*, 17(2), 252;

BERLINGUET, L. and GAUDRY, R., 1952, *J. Biol. Chem.*, 198, 765;

BODANSZKY, M., et al., 1978, *J. Med. Chem.*, 21(10), 1030;

MAURER, P. J. and MILLER, M. J. 1981, *J. Org. Chem. Soc.*, 46(13), 2835;

BIRNBAUM, S. M., LEVINTOW, L. KINGSLEY, R. B. and GREENSTEIN, J. P., 1952, *J. Biol. Chem.*, 194, 455;

COREY, E. J. and VANKATESWARLU, A., 1972, *J. Am. Chem. Soc.*, 94, 6190;

SIEBER, P., 1977, *Helv. Chim. Acta*, 60, 2711 (b);

GERLACH, H., 1977, *Helv. Chim. Acta*, 60, 3039;

MITSUNOBU, O., 1981, *Synthesis*, 1981,1.

Horwitz, et al., have discovered the currently accepted structural nature of Exochelins, and patented uses of the same as novel iron chelators to inhibit the iron mediated oxidant injury which occurs during reperfusion, and have patent applications pending to other hydroxyl radical related insults to living tissues, including cancer, artherosclerosis and vessel occlusion following angioplasty as well as the preservation of organs for transplant. See the above-referenced applications and United States Letters Patents incorporated by reference.

Likewise, the synthesis of related compounds strongly suggests the medical need for, and the production of, synthetic versions of such important and needed compounds. See, for example, HU, J. and MILLER, M. J., "Total Synthesis of a Mycobactin a Siderophore and Growth Promoter of *Mycobacterium Smegmatis*, and Determination of its Growth Inhibitory Activity against *Mycobacterium tuberculosis*", 1997, pp.3462–3468, J. Chem. Soc. 119. However, complications in synthesizing the desired compounds require modifications to known procedures, and various sterochemical constraints have previously prevented generating Exochelins through synthetic routes.

With chelation of iron now being recognized as a means for preventing the oxidative damage of living tissue, the potential applications for Exochelins and related compounds abound. As an iron scavenger in a physiological system capable of withdrawing iron from iron-bearing proteins, Exochelins effectively prevent cell destruction following interruption of blood flow. Similarly, chelation of other metals can regulate levels of the same in various other therapeutic settings, including the delivery of various desirable metals to the body, or the targeting of diseased organs with beneficial drugs bound to Exochelins, or the like synthetic transport means.

Prior work of Horwitz, et al. resulted in purified Exochelins from biological sources and demonstrated their utility as scavengers of free iron and their effectiveness in preventing the formation of tissue damaging hydroxyl radicals or damage to tissue once the hydroxyl radicals are formed. In particular, Horwitz, et al., purified Exochelins from *M. tuberculosis* and demonstrated that they effectively removed iron from transferrin, lactoferrin and ferritin at physiological pH, without transmitting any of the infectious properties of the tuberculosis bacteria. Likewise, Horwitz, et al., were responsible for showing for the first time that these Exochelins block hydroxyl radical formation by the Fenton reaction and, based upon the response of cardiac myocytes, are effective for preventing reperfusion injury after myocardial infarction or vascular insults to other tissue when administered after an attack occurs, in addition to several hours following such an episode.

Further, Horwitz, et al., in elucidating the chemical structure of Exochelins noted that prior references cited above had failed to define the actual structure and, instead, characterizing the Exochelins as peptides. These unsuccessful attempts to identify the actual structure of the Exochelin family likewise have hindered anyone from undertaking or accomplishing their synthesis. By uncovering the broad range of molecular weights which Exochelins exhibit, Horwitz, et al., have discovered that several series of compounds with identifiable differences in molecular weights are properly included with the grouping. Exochelins cannot be considered to be peptides, instead they contain three amino acids and other structural moieties (salicylic acid, dicarboxylic acids or monoester analogs, and hydroxy carboxylic acids) formed by amide (—NH—CO—), hydroxamate (—N(OH)—CO—) and ester condensations (—CO—O).

Likewise, in copending U.S. Ser. No. 08/882,122, now U.S. Pat. No. 5,837,677 deprivation of iron has been shown to attack cancer cells by modes which are particularly well addressed by Exochelins. Owing to their very high affinity for iron and their lipid solubility, Exochelins of, for example, *Mycobacterium tuberculosis*, possess enhanced ability to enter cells. A synthetic iron chelator with lipid solubility clearly would help to address cancer diagnosis, treatment, and screening.

Clearly, there exists a longstanding need for an improved synthetic agent or compound effective for rapidly chelating metals as they become available, to counteract myocardial infarction, and treat cancer and other related medical conditions driven by the presence of free metals, or protect tissue which may be damaged by the hydroxyl radical and related mechanisms imparting cell death and destruction.

OBJECTS AND SUMMARY OF THE INVENTION

Accordingly, it is an object of the invention to provide a process for the synthetic preparation of Exochelins which overcomes the drawbacks of the prior art.

An additional object of the invention is to synthesize a compound which behaves, in all respects, like the natural material isolated by Horwitz, et al.

An additional object of the present invention is to provide a process to prepare synthetic Desferri Exochelin 786SM(R) which rapidly chelates ferric iron in solution.

It is a further object of the invention to provide for the chemical synthesis of Desferri-Exochelin 786SM(R) effective for rapidly binding iron, among other metals.

It is an additional object of the present invention to provide a synthetically prepared Exochelin compound that elutes on reverse-phase HPLC (phenyl column) at the same concentration of acetonitrile as the native molecule.

It is yet still another object of the invention to provide a simplified process design for the generation of synthetic Exochelins on an industrial scale for use in the prevention of oxidative damage to living tissue.

Briefly stated, there is provided a synthetic process for generating Exochelin 786SM(R), a new molecule having a six carbon chain terminating in a methyl ester coupled to an acyclic hydroxamate, with four stereogenic centers, including three S-isoforms and an R-configuration at a B subunit.

According to a feature of the present invention there is provided, a process for the synthesis of Exochelin 786SM (R) comprising the steps of; generating N-(2-benzyloxy-benzoyl)-L-serine, preparing D,L-ε-hydroxynorleucine, producing N-acetyl-D,L-ε-hydroxynorleucine, creating L-N-t-

Boc-ε-hydroxynorleucine, generating O-benzyl methyl suberyl hydroxamate, providing L-N-Boc-ε-bromonorleucine trimethylsilylethyl ester, coupling O-benzyl methyl suberyl hydroxamate with L-N-Boc-ε-bromonorleucine trimethylsilylethyl ester to give L-$N^2$-Boc-$N^6$-Methylsuberyl, $N^6$-(benzyloxy) lysine 2-trimethylsilylethyl ester, removing of the N-tert-butoxycarbonyl protecting group of L-$N^2$-Boc-$N^6$-Methylsuberyl, $N^6$-(benzyloxy) lysine 2-trimethylsilylethyl ester to yield a substituted lysine, and coupling the same with L-N-2-[benzyloxy (benzoyl)]serine, to yield 2-trimethyl silylethyl ester of dibenzyl Exochelic acid, transforming 2-trimethyl silylethyl ester of dibenzyl Exochelic acid to dibenzyl Exochelic acid, preparing benzyl epi-cobactin, forming an ester bond between dibenzyl Exochelic acid and benzyl epi-cobactin; and, hydrogenolytically removing three benzyl groups therefrom, for synthesizing Exochelin 786SM(R).

The above, and other objects, features and advantages of the present invention will become apparent from the following description read in conjunction with the accompanying figures, tables and formulae, outlining and describing a set of embodiments of synthetic processes according to the present invention, wherein like reference designating numerals are employed throughout to represent common chemical species moieties and functional groups.

BRIEF DESCRIPTION OF THE DRAWINGS

These and other features, aspects and advantages of the present invention will become better understood with reference to the following description, appended claims, and accompanying drawings, where:

FIG. 1*a* is the target molecule Exochelin 786SM(R)(1);

FIG. 1*b* is Myobactin S2 (1*b*), shown for comparison purposes;

FIG. 1*c* depicts the target molecule of FIG. 1*a* separated into functional portions, designated as sections A–F, to aid in the description of the various mechanisms further explained as Schemes I–VII below;

FIG. 2 shows the chemical pathway under Scheme I, in accordance with an embodiment of the process for the synthesis of the present invention to form a precursor for a portion of the target molecule;

FIG. 3 shows the chemical pathway under Scheme II, in accordance with an embodiment of the process for the synthesis of the present invention to form a second portion of the target molecule;

FIG. 4 shows the chemical pathway under Scheme III, in accordance with an embodiment of the process for the synthesis of the present invention to form a third portion of the target molecule;

FIG. 5 shows the chemical pathway under Scheme IV, in accordance with an embodiment of the process for the synthesis of the present invention to combine prior produced portions of the target molecule to form a larger portion of said target molecule;

FIG. 6 shows the chemical pathway under Scheme V, in accordance with an embodiment of the process for the synthesis of the present invention to combine prior produced portions to a still larger portion of the target molecule;

FIG. 7 shows the chemical pathway under Scheme VI, in accordance with an embodiment of the process for the synthesis of the present invention to form a last portion of the target molecule;

FIG. 8 shows the chemical pathway under Scheme VII, in accordance with an embodiment of the process for the synthesis of the present invention to combine the portions produced in FIGS. 6 and 7 to generate the target molecule;

FIG. 9 shows the NMR spectrum of (L)-N-Boc-ε-bromonorleucine methyl ester 22.

FIG. 10 shows the NMR spectrum of hydroxamate 20.

FIG. 11 shows the NMR spectrum of L-N-Boc-ε-bromonorleucine 2-trimethylsilylethyl ester (subunit C) 24.

FIG. 12 shows the NMR spectrum of an unwanted end product produced in Scheme IV (FIG. 5)

FIG. 13 shows the NMR spectrum of L-$N^2$-Boc-$N^6$-methylsuberyl, $N^6$-(benzyloxy)lysine 2-trimethylsilylethyl ester 25.

FIG. 14 shows the NMR spectrum of caprolactam (Subunit A) 31.

FIG. 15 shows the NMR spectrum of 2-trimethylsilylethyl-protected dibenzyl Exochelic acid 28.

FIG. 16 shows the Mass Spectrum of 2-trimethylsilylethyl dibenzyl protected Exochelic acid 28.

FIG. 17 shows the NMR spectrum of dibenzyl Exochelic acid 29.

FIG. 18 shows the NMR spectrum of benzyl epi-cobactin 34.

FIG. 19 shows the NMR spectrum of tribenzyl Exochelin 786SM(R) 35.

FIG. 20 shows the NMR spectrum for Exochelin 786SM (R) 1.

FIG. 21 shows the NMR spectrum for Exochelin 786SM (R) 1.

DETAILED DESCRIPTION OF THE INVENTION

The present inventors have discovered, as described in applicants' copending applications and U.S. Letters Patents, that Exochelins have been found to block or significantly reduce oxidative damage to tissue resulting from the iron-mediated catalysis of tissue and free radical reactions mediated by the hydroxyl radical. In particular, such effects have been shown to be at least participative in reperfusion injury, arteriosclerosis cateract formation, cancer and other degredative injuries to living tissue.

Likewise, Exochelins have been shown to effectively prevent, or at least retard, reperfusion injury when administered at the start of, or concurrent with reperfusion, arterial blockage following angioplasty, and reduce the damage to normal tissue resulting from chemotherapy to treat cancer. Further, the present inventors have previously disclosed that the Exochelins comprise a much broader class of materials having a different chemical structure than those originally theorized by Macham et al. and Barclay et al.

Exochelins are now known to chelate a broad range of metals, and when properly modified they can be used to treat specified diseases, attack cancer cells (among others) and assist in diagnostic and monitoring functions by detecting the presence of disease. For example, neuroblastoma cells can be negatively affected by the removal of iron using desferrioxamine with harmful impacts upon healthy tissue. Likewise, chemotherapy, such as used during leukemia, often results in iron overload (as do transfusions) and Exochelins have been shown to be effective for treating the same.

Referring now to the figures, and more particularly to FIGS. 1*a* and 1*b*, the target molecule Exochelin 786SM(R) is shown in comparison and contrast with Mycobactin S2. Although this molecule is similar in structure to Mycobactin S2, there are significant differences. Exochelin 786SM(R) possesses an eight carbon chain terminating in a methyl ester coupled to the acyclic hydroxamate (subunit F, FIG. 1c), while Mycobactin S2 contains only a methyl group at the corresponding position. The other structural variation is stereochemical in nature. Each compound contains four stereogenic centers, and in the case of Mycobactin S2, all of these occur in the S-configuration. Exochelin 786SM(R), however, possesses the R-configuration in subunit B. The three remaining centers occur as the S-isoforms, analogous to Mycobactin S2. These differences require that appropriate modifications of the established procedure be employed in order to synthesize the target molecule.

Referring to FIG. 1c (and in particular to the blocked diagram of functional units of the target molecule designated A–F), the initial goal of the instant synthesis was the preparation of the E/D subunit of Exochelin 786SM(R).

Referring to FIG. 2, Scheme I, the illustrated portion of the synthesis is identical to that employed in the preparation of Mycobactin S2. The first step involved conversion of salicylic acid 2 to benzyl-2-benzyloxybenzoate 3, using benzyl chloride and anhydrous potassium carbonate in refluxing N,N-dimethylformamide (DMF) according to Farkas, et al. The crude product was then hydrolyzed with methanolic sodium hydroxide to give 2-benzyloxybenzoic acid 4 in 95% overall yield.

2-Benzyloxybenzoic acid 4 was then reacted with p-nitrophenol 5 and dicyclohexylcarbodiimide (DCC) in ethyl acetate to produce, after work-up, 4-nitrophenyl-2-(benzyloxy)benzoate 6 in 45% yield. Treatment of the benzoate 6 with L-serine 7 and triethylamine (TEA) in tetrahydrofuran (THF)/water gave the protected E/D fragment 8 of Exochelin 786SM(R) in 79% yield. This segment undergoes subsequent reaction with a protected form of the C/F fragment to generate the largest subunit of the target compound.

Referring now to FIG. 3, the next goal of the synthesis according to the present invention was the preparation of the key component of the A and C subunits of Exochelin 786SM(R). Both of these fragments contain the same basic building block, L-ε-hydroxynorleucine 14.

As discussed above, the route according to a preferred embodiment of the process of the present invention employs the amino acid L-ε-hydroxynorleucine as the primary synthon. The synthesis utilizes cheap, readily available asymmetric starting materials to prepare racemic-hydroxynorleucine DL-14. Enzymatic resolution yields the L-isomer which is subjected to various protection and coupling reactions to give the required fragments of Exochelin 786SM(R).

The first step of the procedure shown in Scheme II (FIG. 3) is the aqueous hydrolysis of 3,4-dihydro-2H-pyran 9 catalyzed by hydrochloric acid. The intermediate aldehyde 10 which results is treated with sodium bisulfite (primarily $Na_2S_2O_5$ which yields two equivalents of $NaHSO_3$ upon dissolution in water) after neutralization to form the bisulfite addition product 11 which is then treated with potassium cyanide in situ to generate cyanohydrin 12. This material was isolated utilizing slightly different extractive work-ups and treated with ammonium carbonate in water to produce pure hydantoin 13 in one instance a yield of 42.5% and in the second instance, 37% yield. A sample of the hydantoin 13 was hydrolyzed in an autoclave at approximately 126° C. with aqueous barium hydroxide to produce a 38% yield of pure D,L-ε-hydroxynorleucine DL-14, following work-up and recrystallization from water/isopropanol. Verification of the composition was accomplished by elemental analysis at an independent laboratory.

D,L-ε-hydroxynorleucine DL-14 was reacted with p-nitrophenyl acetate 15 and triethylamine (TEA) in aqueous solution to generate N-acetyl-D,L-ε-hydroxynorleucine 16. This material was somewhat contaminated, presumably with triethylamine hydrochloride from the neutralization process, however a pilot resolution reaction demonstrated that relatively pure L-ε-hydroxy-norleucine could be obtained from the impure N-acetate. The reaction was scaled-up and approximately 360 grams of crude N-acetyl-D,L-ε-hydroxynorleucine 16 were produced.

Historically, racemic N-acetyl-hydroxynorleucine has been resolved to L-ε-hydroxy-norleucine via enzyme catalyzed hydrolysis utilizing hog kidney Acylase. Those having skill in the art have routinely used Acylase I from *Aspergillus* species for resolutions, and have found that the enzyme from this source works equally well for the target reaction. The product, L-ε-hydroxynorleucine, was shown to be enantiomerically pure by chiral thin-layer chromatography (no D-isomer is detected), however the less-polar impurity was still present in the material (<5%) as shown by Silica Gel chromatography. This is supported by the optical rotation data.

L-ε-hydroxynorleucine L-14 was treated with di-tert-butyl dicarbonate and triethylamine in tetrahydrofuran/water to block the N-terminus of the amino acid as the BOC derivative for future synthetic manipulations. The reaction was run in three batches and generated approximately 40 g of N-t-BOC-L-ε-hydroxynorleucine L-17. The cumulative yields for the batches were 17.6, 31.1, and 30% for three steps of the sequence starting from amino acid DL-14. The first two samples of material (1.5 and 13.5 grams) were shown to be >99% pure by thin-layer chromatography and optically pure by optical rotation data. A sample of the BOC derivative was hydrolyzed with trifluoroacetic acid to insure that racemization had not occurred. CHIRALPLATE™ chromatographic analysis of the resulting amino acid confirmed that the product was the optically pure L-isomer.

Referring now to FIG. 4 (Scheme III), the preparation of the F portion was accomplished by reacting O-benzylhydroxylamine hydrochloride 18 with methyl suberyl chloride 19 in THF in the presence of excess pyridine. Standard workup and product isolation gave a 95% yield of crude hydroxamate 20 which by TLC and $^1$H NMR analyses was judged to be sufficiently pure for use in a subsequent coupling with subunit C.

Figure 5:
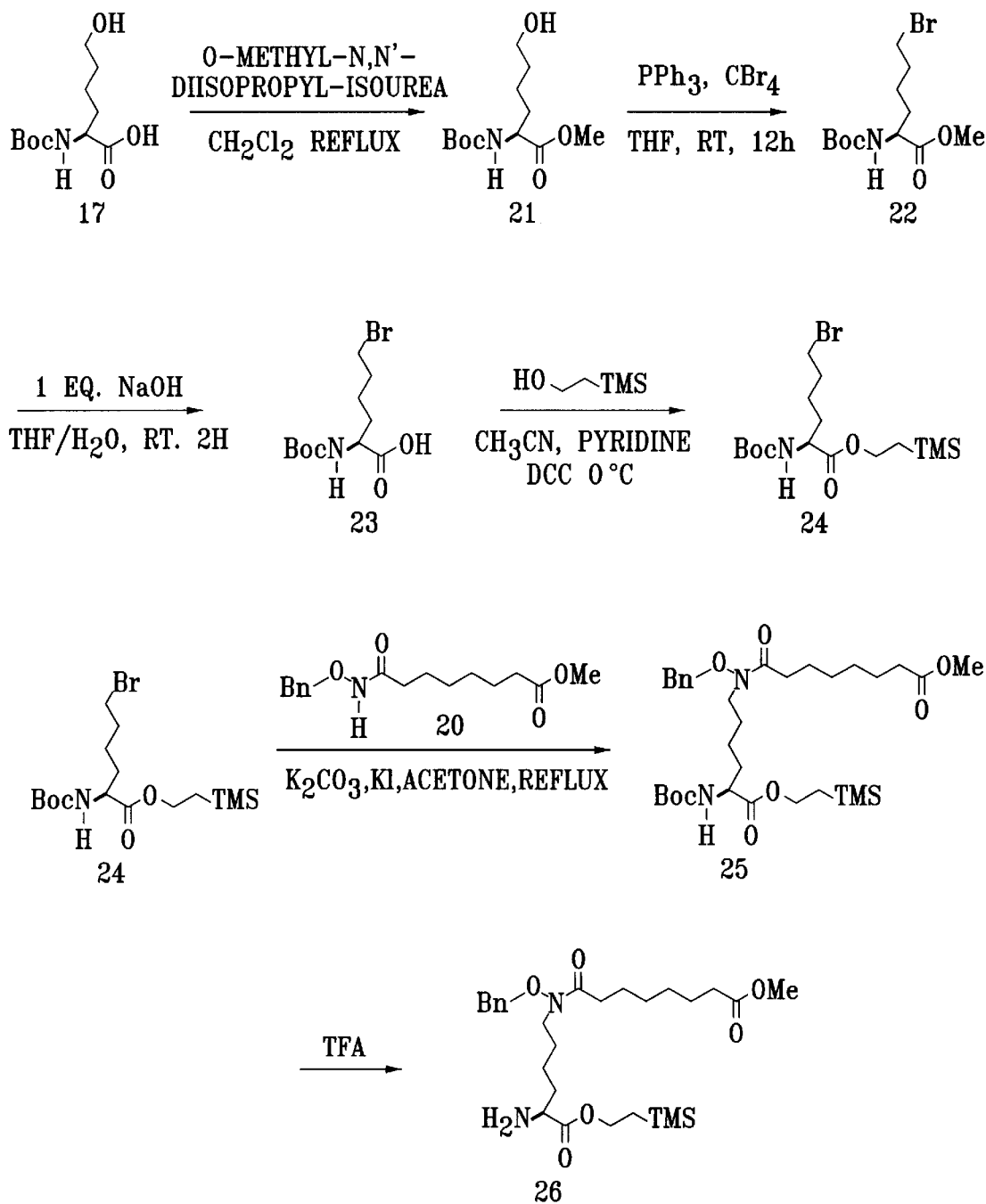
Figure 9:
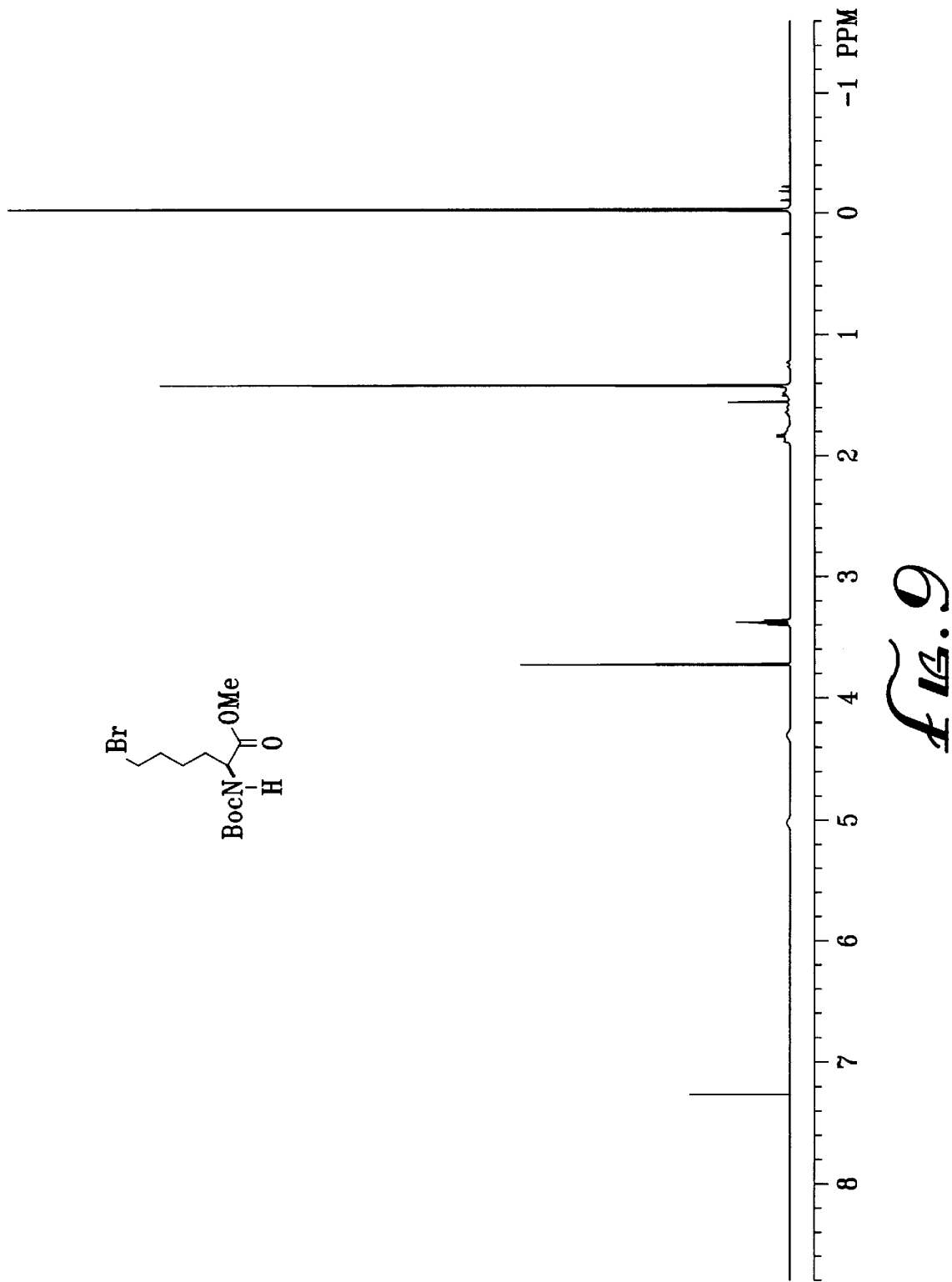

Referring now to FIG. 5 (Scheme IV), the previously prepared N-t-Boc-L-ε-hydroxynorleucine 17 was reacted with O-methyl-N,N'-diisopropylisourea to give the crude methyl ester product 21. This product was reacted, without further purification, with triphenylphosphine/carbon tetrabromide in THF followed by chromatographic purification to give L-N-Boc-ε-bromonorleucine methyl ester 22. The yield for these two steps was 71%. This material was shown by $^1$H NMR and optical rotation analyses to be identical to that reported in the literature. See FIG. 9.

Maurer and Miller have shown the use of the methyl ester 22 as a protected intermediate in their synthesis of Mycobactin S2. However, synthetic complications arise as a result of competing reactions during subsequent manipulations of the protected C/F fragment to form the Exochelin 786SM (R). The coupling of intermediates 20 and 22 would not be adversely affected by the F portion methyl ester. On the other hand, the carboxyl group in 22 must be converted to an appropriately protected analogue which is robust enough to survive the required synthetic manipulations, yet can be selectively deprotected in the presence of the F portion ester.

Conversion of methyl ester 22 into the corresponding acid 23 was accomplished by saponification of the ester in tetrahydrofuran/water at room temperature for two hours to give a 94% yield of the desired acid.

The conversion of the acid to 2-trimethylsilylethylester 24 was next accomplished according to the procedure of Sieber. Reaction of acid 23 with 2-(trimethylsilyl)ethanol in the presence of 1,3-dicyclohexylcarbodiimide/pyridine in acetonitrile gave, after workup and chromatographic purification, a 92% yield of the desired ester 24.

With the appropriately protected ester 24 (subunit C) and hydroxamate 20 (subunit F) in hand, coupling to form the C/F fragment was accomplished according to Scheme IV under the reaction conditions as described by Maurer and Miller. The ester 24 was reacted with the hydroxamate 20 in the presence of 0.2 equivalent of potassium iodide and 2.5 equivalent anhydrous potassium carbonate in refluxing acetone overnight.

After 24 hours, an additional 0.3 equivalent of potassium iodide was added and the reaction mixture vigorously stirred and refluxed. After 120 hours, the reaction mixture was filtered, concentrated, and resubjected to treatment with fresh reagents at reflux overnight. The reaction mixture was again filtered and concentrated and the resulting residue was subjected to chromatographic purification yielding three fractions.

The first fraction eluted was shown by TLC and $^1$H NMR to be recovered starting material, L-N-Boc-ε-bromonorleucine 2-trimethylsilylethyl ester 24. The second fraction was shown by $^1$H NMR analysis to be approximately a 9:1 mixture of, presumably, hydroximate by-products. $^1$H NMR analysis indicated that the third fraction was the desired product 25. The yield of the desired N-alkylated product was 78%, taking into account recovered starting material.

Although the reaction did not reach completion after extended time, the 78% yield is acceptable (Maurer and Miller reported a 65% yield for the analogous reaction). Additionally, the ratio of N- to O-alkylation is nearly 8:1, whereas a 5:1 ratio is reported by Maurer and Miller. Finally, removal of the N-tert-butoxycarbonyl protecting group of 25 was affected by brief treatment with trifluoroacetic acid to give substituted lysine 26.

Figure 6:
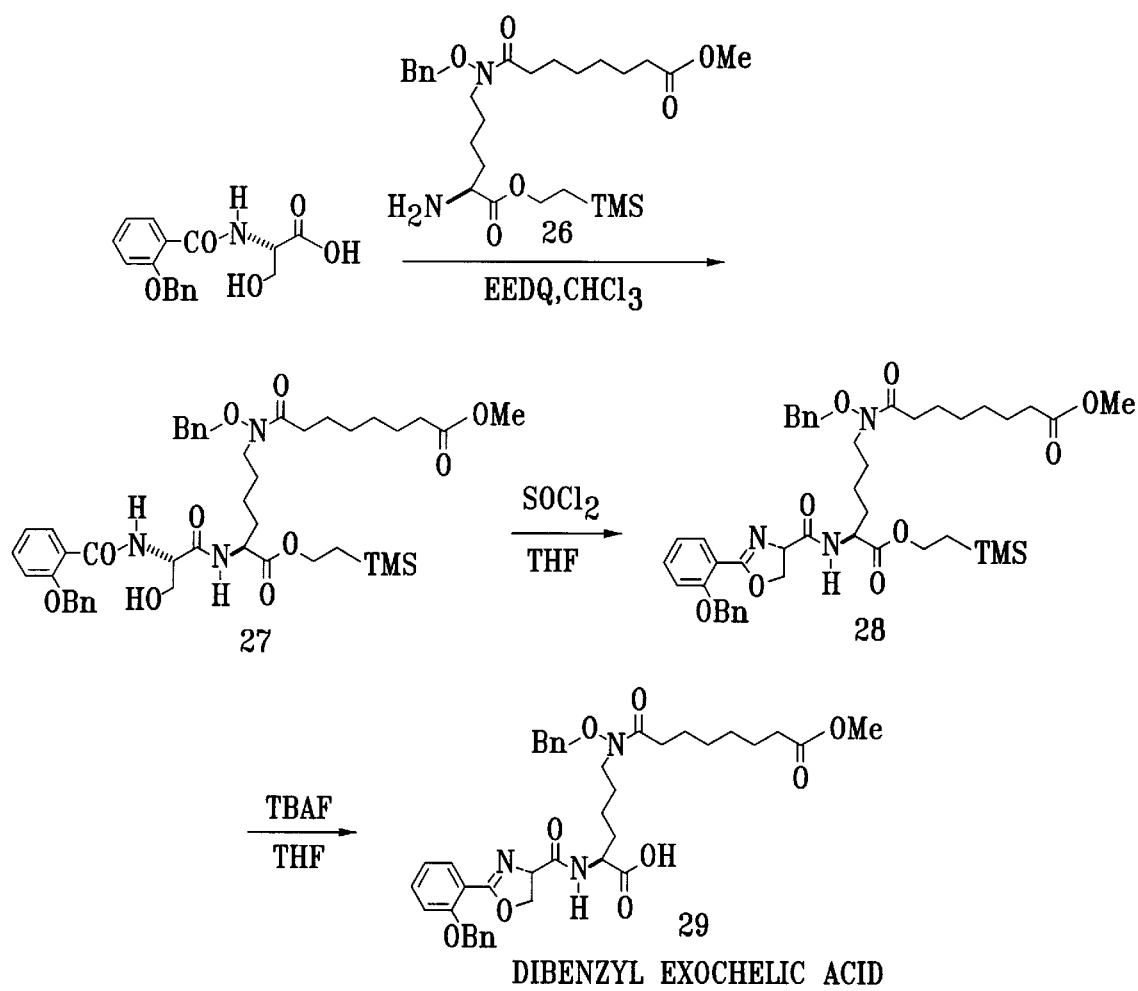

Referring now to FIG. 6 (Scheme V), the coupling of the C/F and E/D fragments and subsequent transformation to dibenzyl Exochelic acid 29 was accomplished. Previously prepared C/F portion 26 was coupled with protected E/D 8 using 2-ethoxy-N-(ethoxycarbonyl)-1,2-dihydroquinoline (EEDQ) in chloroform. Standard workup and product isolation gave a 72% yield of crude dipeptide 27. Dehydrative cyclization of the substituted serine residue was achieved via treatment with thionyl chloride to produce oxazoline 28 in 56% yield after chromatographic purification. The structure of this molecule, the 2-trimethylsilylethyl ester of dibenzyl Exochelic acid, was verified by mass spectral and $^1$H NMR analyses.

The transformation of compound 28 to dibenzyl Exochelic acid 29 required the selective removal of the 2-trimethylsilylethyl ester in the presence of a variety of functionalities including two chiral centers which could potentially undergo racemization.

A first attempt involved treating a tetrahydrofuran solution of the ester 28 with two equivalents of tetrabutylammonium fluoride (TBAF). After one hour at room temperature, TLC analysis indicated the complete absence of starting material and the appearance of one major new spot. Workup and product isolation gave a light tan glass in 74% yield. This crude product was subjected to $^1$H NMR analysis which indicated that the desired reaction gave dibenzyl Exochelic acid 29. The $^1$H NMR, although contaminated by a small amount of tetrabutylammonium salt, showed the material to consist primarily of a single component with no indication of any by-products from side reactions, including racemization.

The remainder of ester 28 was treated with TBAF, the crude product combined with that from the small scale test reaction, and the material purified by Silica Gel chromatography to give pure dibenzyl Exochelic acid 29 as a clear colorless glass in 54% yield.

Figure 7:
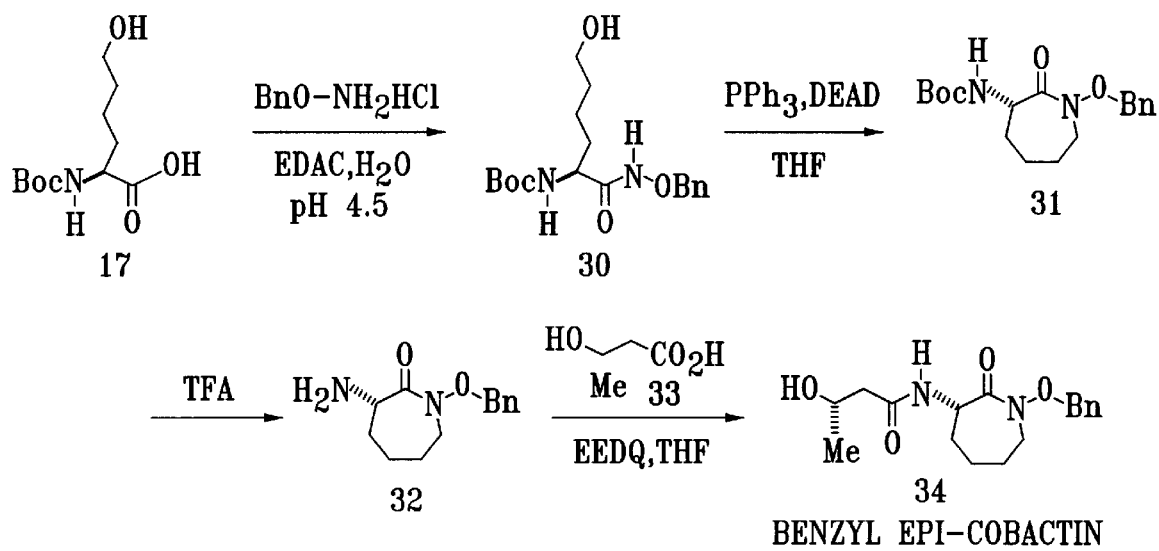

Referring now to FIG. 7 (Scheme VI), the A/B fragment, benzyl epi-cobactin 34 was prepared in the manner reported by Mauer and Miller. The synthesis of the subunit A involved conversion of the carboxyl group of previously prepared L-N-t-Boc-ε-norleucine 17 to O-benzylhydroxamate 30, followed by cyclization to caprolactam 31.

L-N-Boc-ε-norleucine was reacted with O-benzyl-hydroxylamine in aqueous solution at pH 4.5 using 1-ethyl-3-(dimethylamino)propylcarbodiimide hydrochloride (EDAC) as the coupling agent. Pure product was obtained from two separate reactions. An alternative non-aqueous procedure for preparing the hydroxamate provided a yield of only 60%.

Hydroxamate 30 was treated with triphenylphosphine and diethyl azodicarboxylate in anhydrous tetrahydrofuran to induce cyclization to caprolactam 31. The reaction produces a mixture of products which was fractionated by medium-pressure liquid chromatography (MPLC) on Silica Gel. The principal fraction was shown to contain two major components (52% and 35%) by reversed-phase high-pressure liquid chromatography (HPLC). The desired product was obtained in 97% pure form by a combination of Silica Gel column chromatography and recrystallization from hexanes. Structure verification was determined by $^1$H NMR and mass spectral analyses.

Removal of the N-tert-butoxycarbonyl (N-t-BOC) protecting group of 31 by brief treatment with trifluoroacetic acid gave the free amine 32 which was subsequently coupled to S-(+)-3-hydroxybutyric acid 33 using EEDQ. Acid 33 was previously obtained by continuous ether extraction of an acidified aqueous solution of its sodium salt. Purification of the crude coupled product by recrystallization from ethyl acetate/ether resulted in a 78% yield of benzyl epi-cobactin 34.

Figure 8:
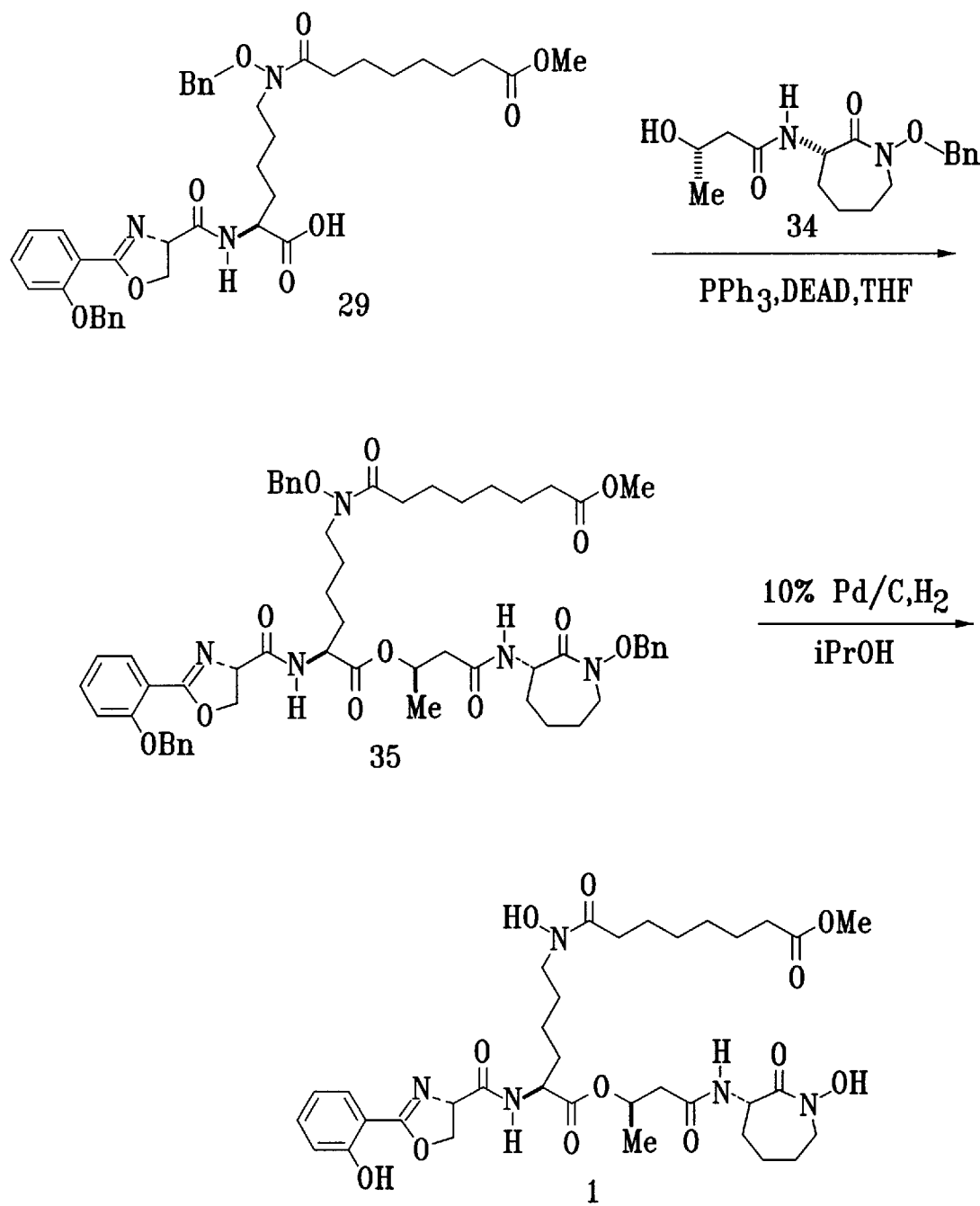

Referring now to FIG. 8, the final steps of the synthesis of Exochelin 786SM(R) 1 consisted of forming an ester bond between dibenzyl Exochelic acid 29 and benzyl epi-cobactin 34, followed by hydrogenolytic removal of the three benzyl groups as shown in Scheme VII.

Using a slight modification of the procedure of Maurer and Miller, triphenyphosphine/DEAD-mediated ester bond formation proceeded as desired and tribenzyl Exochelin 786SM(R) 35 was isolated in 61% yield. Literature precedent indicates that this process results in inversion at the hydroxyl carbon of 34 during ester formation. This yields the R-configuration at that center in compound 35, and leads to the required overall stereochemistry of the molecule; S,S,R,S. Finally, hydrogenolysis of the benzyl groups of 35 provided 24 mg of Exochelin 786SM(R) 1 in approximately 98% pure form based upon $^1$H NMR, TLC and HPLC analyses.

The present inventors have demonstrated that the target molecule, Exochelin 786SM(R), can be synthesized on laboratory scale. The key intermediate of the overall synthetic scheme is N-t-BOC-L-ε-hydroxynorleucine 17 since it is the primary building block of two of the major subsections of Exochelin 786SM(R). The yields encountered during the construction of this compound are substantially lower than those reported in the literature. Furthermore, half of the material is unavoidably lost towards the end of the pathway as a result of the resolution; the undesired D-isomer is simply "discarded" at this point.

In sum, the synthetic process of the present invention has resulted in generation of a compound having an alkyl chain terminating with a methyl ester moiety, among other things, and this differentiates the instant synthesis from those conducted relating to Mycobactin S2 and related compounds. Further, the synthetic molecule was compared to the native Exochelins yielding results which confirm the objects of the present synthesis have been achieved. By way of example, the present inventors have undertaken functional studies, summarized below regarding the target molecule.

Functional Studies of Synthetic Desferri-Exochelin 786SM (R)

Capacity to Chelate Iron

To determine if the synthetic desferri-Exochelin 786SM (R) could chelate iron, as does the native form, we dissolved the Exochelin in 0.1% TFA containing ferric ammonium citrate at a 10-fold molar excess of iron to Exochelin. We then loaded the solution on a Bondapak Phenyl 125 Å 10 μm (3.9×300 mm) HPLC column and subjected the Exochelin to reverse-phase HPLC (High Pressure Liquid Chromatography) on a Rainin (Woburn, Mass.) HPXL system. The Exochelin was eluted with a 0–100% gradient of a buffer consisting of 0.1% TFA and 50% acetonitrile at a flow rate of 1 ml/min. The ferri-Exochelins were monitored at 200-nm and 450-nm absorbance. The mass of ferri-Exochelins was assayed by measuring the area under the peak at 450-nm and using a conversion factor derived from assaying known amounts of ferri-Exochelins.

In the absence of ferric ammonium citrate, only a small amount of ferri-Exochelin was eluted from the HPLC column, amounting to 2.16% of the Exochelin added. In the presence of ferric ammonium citrate, 100% of the Exochelin eluded from the column in the ferri form.

Thus, desferri-Exochelin 786SM(R) rapidly chelates ferric iron in solution.

Elution Profile on Reverse-Phase HPLC

Synthetic Exochelin 786SM(R) and native Exochelin 784SM(R) were diluted in water containing 0.1% TFA and excess ferric ammonium citrate and individually loaded on a phenyl column as described above. The Exochelins were eluded with a 0–100% gradient of a buffer consisting of 0.1% TFA and 50% acetonitrile at a flow rate of 1 ml/min on a Rainin (Woburn, Mass.) HPXL system. The Exochelins were identified by their 450-nm absorbance.

Native Exochelin 786SM(R) elutes just ahead of native Exochelin 784SM(R) (i.e. at a concentration of acetonitrile approximately 0.5% less than that at which 784SM(R) elutes. To determine if synthetic Exochelin 786SM(R) elutes the same place relative to native Exochelin 784SM(R), we ran these Exochelins on the phenyl column individually and together. Synthetic Exochelin 786SM(R) eluted precisely where the native Exochelin 786SM(R) would have eluted at a concentration of acetonitrile approximately 0.5% less than at which native Exochelin 784SM(R) eluted.

Thus, synthetic desferri-Exochelin 786SM(R) has the same elution profile on reverse-phase HPLC as native Exochelin 786SM(R).

The examples below set forth specific methods used to prepare intermediates, including all above referenced synthons, and provide guidance to those skilled in the art on use of the instant teachings to facilitate generation of multigram quantities of Exochelin 786SM(R) in accordance with the teachings of the present invention. No limitations on applicants' claimed subject matter are intended thereby, or by the accompanying 13 graphical presentations of data further comprising spectroscopic analysis and elution profiles, which are appended to the specification of the present invention for the purpose of demonstrating a preferred embodiment of applicants' novel process.

EXAMPLES

The various steps to prepare the target compound are set forth below.

Optical rotations for all materials were measured at the 589 (D) line of sodium at ambient temperatures on a Rudolph Research Autopol III polarimeter in a 5 cm cell, and are expressed in grams solute per 100 ml of solution. Thin-layer chromatographic analyses (TLC) were performed on pre-coated aluminum sheets of Silica Gel 60 $F_{254}$ (E. Merck) and on pre-coated glass sheets (0.25 mm) of Silica Gel RP modification coated with $Cu^{+2}$ and chiral reagent (CHIRALPLATE™, Macherey-Nagel). Medium-pressure liquid chromatography (MPLC) was performed on a 2.5 cm×46.0 cm glass column containing Silica Gel (230–400 mesh, grade 60) using a FMI Model RP-SY pump. High-pressure liquid chromatography (HPLC) was performed on a Rainin dual pump system (Dynamax Model SD-200) with UV detection (Rainin Model UV-C) at 254 nm. All commercial reagents and solvents used in this study were reagent grade.

A. Benzyl-2-benzyloxybenzoate, 3:

Anhydrous potassium carbonate was ground to a fine powder with a mortar and pestle, transferred to a porcelain crucible, and heated over a Bunsen burner for 1.0 hr. This material was transferred to a stoppered roundbottom flask.

A 1-L 3-necked roundbottom flask equipped with a mechanical stirrer, a condenser fitted with a gas bubbler, and a stopper was flushed with dry nitrogen and charged with 20.0 g (0.145 moles) of salicylic acid 2, 58.0 g (0.458 moles) of benzyl chloride, 450 ml of anhydrous dimethylformamide, and 90.0 g (0.651 moles, freshly powdered and heated as above) of anhydrous potassium carbonate. The mixture was stirred and heated at reflux under nitrogen for 1.5 hrs, cooled to room temperature, and poured into 2.5 L of ice/water. The solution was stirred for 30 min, vacuum filtered using a Buchner funnel, and the resulting white solid washed with ice cold water (3×100 ml).

The solid was dissolved in 250 ml of dichloromethane, transferred to a 500-ml separatory funnel, washed with water (1×100 ml) and saturated brine (1×100 ml), and the dichloromethane layer dried over anhdrous magnesium sulfate. The solution was vacuum filtered through a coarse sintered-glass funnel and concentrated in vacuo to yield 53.8 g (116.7%) of a yellow oil that solidified to an off-white solid at 3° C. TLC (same conditions as above) shows one major product, $R_f$ 0.43.

The above process was repeated with 26.2 g (0.190 moles) of salicylic acid, 76 g (0.600 moles) of benzyl chloride, 500 ml of anhydrous dimethylformamide, and 118.0 g (0.854 moles, freshly powdered and heated as above) of anhydrous potassium carbonate.

The mixture was then handled as above yielding 68.1 (112.7%) g of a yellow oil that solidified to an off-white solid at 3° C. TLC (same conditions as above) shows one major product, $R_f$ 0.43. The two preparations were then combined to provide 121.9 g of crude benzyl-2-benzyloxybenzoate 3.

B. 2-Benzyloxybenzoic acid, 4:

A 2-L roundbottom flask equipped with a magnetic stirring bar and a condenser fitted with a gas bubbler was flushed with nitrogen and charged with 875 ml of methanol, 160 ml (1.600 moles) of 40% aqueous sodium hydroxide, and the 121.9 g (theoretical—0.334 moles) of crude benzyl-2-benzyloxybenzoate 3. The solution was stirred under nitrogen and heated at reflux for 2.5 hrs, cooled, concentrated in vacuo, and the resulting solid dissolved in 1.5 L of water. The solution was vigorously stirred and acidified to pH 1.0 with concentrated hydrochloric acid. An oil separated and was solidified by cooling in an ice/water bath for 2.5 hours. The solid was isolated by vacuum filtration, washed with cold water (500 ml), air dried, and then vacuum dried to yield 78.5 g of crude product. This material was dissolved in 200 ml of hot ethyl acetate, and the resulting cloudy solution treated with 2 g of anh. magnesium sulfate and vacuum filtered through a coarse sintered-glass funnel. The clear yellow solution was treated with hot hexanes to the cloud point and cooled with stirring to –20° C. where it was held for 18 hrs. The resulting crystalline product was isolated by vacuum filtration using a Buchner funnel, washed with 50 ml of hexanes, and dried under vacuum to yield 72.4 g of a white solid identified as 2-benzyloxybenzoic acid 4 which is a yield of 95.0% based on the 46.2 g of starting salicylic acid 2.

C. 4-Nitrophenyl-2-(benzyloxy)benzoate, 6:

A 500-ml roundbottom flask equipped with a magnetic stirring bar and a stopper was charged with 10.0 g (43.81 mmoles) of 2-benzyloxybenzoic acid 4 from B above, 6.7 g (48.16 mmoles) of p-nitrophenol 5, and 250 ml of ethyl acetate while being cooled in an ice/water bath at 0–3° C. All of the solids had dissolved after 15 min of stirring. Dicyclohexylcarbodiimide (9.94 g, 48.18 mmoles) was added to the mixture and the solution stirred at 0–3° C. for 30 min, followed by room temperature mixing for 4 hrs. The solution was transferred to a 500-ml separatory funnel, washed with 10% aqueous sodium carbonate (4×50 ml), dried over anhydrous magnesium sulfate, filtered through a coarse sintered-glass funnel, and concentrated in vacuo to a crude solid.

This crude solid was dissolved in 200 ml of hot ethyl acetate and treated with 400 ml of hot hexanes, cooled slowly to room temperature then in the freezer at –20° C. for 18 hrs. The crystalline solid was isolated by vacuum filtration using a Buchner funnel, washed with c. 100 ml of hexanes, and dried (air/vacuum) to give 6.10 g of the product. This material was dissolved in 100 ml of hot ethanol (200 proof), cooled slowly to room temperature then in the freezer (–20° C.) for 4 hrs, vacuum filtered using a Buchner funnel, washed with –20° C. ethanol (1×15 ml), and dried (air/vacuum) to give 5.86 g of final product (38.3%).

A second larger batch was then made in a similar manner. A 1-L roundbottom flask equipped with a magnetic stirring bar and a stopper was charged with 25.0 g (109.53 mmoles) of 2-benzyloxybenzoic acid, 16.8 g (120.77 mmoles) of p-nitrophenol, and 625 ml of ethyl acetate. The flask was cooled in an ice/water bath at 0–3° C., and the mixture stirred for 15 min during which time all of the solids had dissolved. Dicyclohexylcarbodiimide (25.0 g, 121.17 mmoles) was added in one portion and the solution stirred at 0–3° C. 1 hr, then at room temperature for 4 hrs. The solution was transferred to a 1-L separatory funnel, washed with 10% aqueous sodium carbonate (4×100 ml), dried over anhydrous magnesium sulfate, filtered through a coarse sintered-glass funnel, and concentrated in vacuo to a crude solid. This material was dissolved in 170 ml of hot ethanol (200 proof), cooled slowly to room temperature then in the freezer at –20° C. for 18 hrs. The crystalline solid was isolated by vacuum filtration using a Buchner funnel, washed with 30 ml of –20° C. ethanol, and dried (air/vacuum) to give 17.28 g of product (45.12%). Melting point=99–100° C. The products of both reactions were combined to provide 23.14 g. of 4-Nitrophenyl-2-(benzyloxy)benzoate, 6.

D. L-N-[2-benzyloxy (benzoyl)] serine, 8:

A 2-L roundbottom flask equipped with a magnetic stirring bar and a stopper was charged with 13.0 g (37.21 mmoles) of 4-nitrophenyl-2-(benzyloxy)benzoate 6 produced in C above, 3.913 g (37.23 mmoles) of L-serine 7, 10.35 ml (74.22 mmoles) of triethylamine, 540 ml of water, and 740 ml of tetrahydrofuran. The mixture was stirred at room temperature for 24 hrs, concentrated in vacuo to remove tetrahydrofuran, and the residual aqueous solution treated with 6N aqueous hydrochloric acid to pH 5.3 (using a pH meter). The solution was transferred to a 1-L separatory funnel, extracted with ether (3×100 ml), and the aqueous layer further acidified with 6N aqueous hydrochloric acid to pH 2.3. The solution was cooled in an ice/water bath for 2 hrs, the white precipitate isolated by vacuum filtration using a Buchner funnel, washed with cold water (3° C., 3×25 ml), and dried (air/vacuum) to yield 9.24g of L-N-[2-benzyloxy (benzoyl)] serine, 8, a white crystalline solid (78.8%) with a melting point of 130–131.5° C. completing Scheme I (FIG. 2).

E. Hydantoin, 13:

A 2-L roundbottom flask equipped with a magnetic stirring bar and a condenser was charged with 100.0 g (1.189 moles) of dihydropyran 9 and 400 ml of 0.02N aqueous hydrochloric acid. The two-phase mixture was heated and vigorously stirred for approximately 15 min at which time a single phase slightly yellow solution resulted. The flask was removed from the heat, stirred an additional 15 min, and neutralized (pH 7.0) with 0.4N aq. sodium hydroxide. The stirred solution was cooled in a water bath and treated with 125 g (0.658 moles) of sodium bisulfite in three portions over 5 min keeping the temperature of the reaction mixture at room temperature. After all of the bisulfite had dissolved, the solution was stirred for 10 min, treated over a 30 min period with the dropwise addition of 78.0 g (1.200 moles) of potassium cyanide in 100 ml of water, and stirred another 30 min at room temperature. The solution was transferred to a 2-L separatory funnel and extracted with dichloromethane. Three distinct layers (a product layer, an aqueous layer, and a dichloromethane layer) were formed and separated.

The dichloromethane fraction was shown by TLC to contain several impurities along with product. The aqueous layer was extracted with diethyl ether (4×250 ml), the extracts combined with the original product layer, and the resulting mixture concentrated in vacuo. The residue was stirred with 230 g (2.394 moles) of ammonium carbonate dissolved in 400 ml of water at 50–55° C. for 1 hr, treated with 10 g of activated charcoal at boiling for 10 min, and vacuum filtered through a Buchner funnel. The filtrate was concentrated in vacuo and the residue dissolved in 300 ml of water (total volume). The solution was cooled to room temperature with stirring and then further cooled at 3° C. for 18 hrs. The crystallized solid was isolated by vacuum filtration, washed with cold water (3×50 ml), and dried to give 87.0 g of hydantoin 14 (42.5%). TLC: Silica Gel, solvent system—acetonitrile/t-butanol/toluene/acetic acid/water (1:1:1:1:1, v/v/v/v/v) or ABTAW; visualization—(1)

ninhydrin, heat followed by (2) 4% phospho molybdic acid/ethanol, heat. Single component, $R_f$ 0.58.

The process was repeated as follows: A 3-L roundbottom flask equipped with a magnetic stirring bar and a condenser was charged with 169.4 g (2.014 moles) of dihydropyran and 700 ml (0.014 moles) of 0.02 N aqueous hydrochloric acid, and the two-phase mixture heated at reflux for 1 hr. After 15 min, the solution is homogeneous. The reaction mixture is cooled to RT with the aid of a cold water bath, treated with 0.4N aq. sodium hydroxide to pH 7.0 while maintaining the temperature at RT. The solution was treated with 212 g (1.115 moles) of sodium bisulfite in 3 portions over 15 min at RT, stirred for 30 min, and treated over 40 min with the dropwise addition of 132.0 (2.027 moles) of potassium cyanide dissolved in 170 ml of water at RT. The solution was stirred for 2 hrs, transferred to a 2-L separatory funnel, and the layers separated. The aqueous layer was extracted with diethyl ether (5×500 ml). The extracts were combined, concentrated in vacuo, and the residue combined with the original organic layer.

This material was treated with 390.0 g (4.059 moles) of ammonium carbonate dissolved in 900 ml of water and stirred for 2 hrs at 55–60° C. The mixture was treated with 16 g of activated charcoal at boiling for 15 min and hot filtered using a Buchner funnel. The yellow filtrate was concentrated in vacuo, the residue dissolved in 500 ml of hot water, cooled to RT with vigorous stirring, and at 0–3° C. in an ice/water bath for 2 hrs. Vacuum filtration, cold water (3×75 ml) washing, and drying yields 168.14 g (48.5%). TLC: ABTAW, (see above) produced one major component at $R_f$ 0.55 and a minor component at $R_f$ 0.31. The crude product was dissolved in 400 ml (total volume) of hot water, cooled to RT with stirring, cooled in an ice/water bath for 2 hrs, filtered, washed with cold water (3×75 ml), and dried to give 142.5 g of hydantoin. This material still contained 5% impurity, therefore, the recrystallization procedure was repeated to give 127.5 g (36.8%) of pure hydantoin 13.

F. D. L-ε-hydroxynorleucine, 14:

Three attempts were made to hydrolyze hydantoin 13 to amino acid. A 1-L Erlenmeyer flask equipped with a magnetic stirring bar was charged with 15.0 g (87.12 mmoles) of the hydantoin 13, 53.0 g (168.00 mmoles) of barium hydroxide octahydrate, and 250 ml of water and heated at boiling for 2–3 min. The solution was autoclaved for 1 hr at c. 126° C. and 18 psi, cooled, filtered through a coarse sintered glass funnel, and the filtrate treated with 11.0 g (114.48 mmoles) of powdered ammonium carbonate. The slurry was stirred at RT for 30 min, filtered as before, and the filtrate concentrated in vacuo. Additional precipitate formed, therefore the solution was re-filtered. The filtrate was concentrated with vigorous stirring on a stirring/hot plate maintaining a volume of c. 250 ml by the addition of hot isopropyl alcohol. The solution was removed from the hot plate at the onset of crystallization, cooled to room temperature, then in the freezer for 18 hrs. The product was isolated by vacuum filtration, washed with cold (3° C.) isopropyl alcohol, and dried (air/vacuum) to yield 4.85 g (37.9%) of amino acid. Melting Point=252–253° C. (decomposition, uncorrected). TLC/ABTAW, produced a single component at $R_f$ 0.27. Elemental analysis (Atlantic Microlab)—calculated for $C_6H_{13}NO_3$ (M.W. 147.17) Calculated: C, 48.97 H, 8.90 N, 9.52 Found: C, 48.80, 8.73 N, 9.40. A second crop of amino acid (4.0 g, 31.3%) was isolated and shown by TLC to contain an impurity (c. 5–10%, $R_f$ 0.50 in ABTAW as above).

A 2.8-L Erlenmeyer flask equipped with a magnetic stirring bar was charged with 87.0 g (0.389 moles) of hydantoin 13, 203.0 g (0.643 moles) of barium hydroxide octahydrate, and 1 L of water. The solution was stirred and heated to boiling for 2–3 min, autoclaved at c. 126° C. and 18 psi for 1 hr, cooled to c. RT, and filtered through a coarse sintered-glass funnel. The filtrate was stirred with 39.0 g (0.406 moles) of powdered ammonium carbonate for 1.5 hrs at RT, filtered as above, the filtrate concentrated in vacuo to c. 500 ml, re-filtered, and the filtrate concentrated in vacuo. The residue was dissolved in 250 ml of water, concentrated to c. 100 ml total volume, and 500 ml of hot absolute ethanol was added with vigorous stirring. The solution was cooled to RT, at 3° C. for 14 hrs, and at −20° C. for 2 hrs, filtered, washed with −20° C. ethanol (3×100 ml) and diethyl ether (3×50 ml), air and vacuum dried to yield 61.71 g of amino acid as a white crystalline solid. TLC/ABTAW produced one major component at $R_f$ 0.27 and a minor (c.5%) component at $R_f$ 0.50. This material was recrystallized from c. 150 ml (total volume) of hot water treated with hot isopropanol (c. 290 ml) to the cloud point. The solution was cooled to RT, then at −20° C. overnight, filtered, washed with cold isopropanol (3×100 ml) and RT ether (3×100 ml), and air/vacuum dried to give material that still contained the impurity. The amino acid was subjected to multiple recrystallization procedures (isopropanol/water, methanol/water, ethanol/water), however, the impurity was never removed. The mother liquors from the various recrystallizations were combined, concentrated in vacuo, and the recovered amino acid mixture saved.

Two 2-L Erlenmeyer flasks equipped with magnetic stirring bars were charged with 63.75 g (0.370 moles) of hydantoin 13, 187.2 g (0.593 moles) of barium hydroxide octahydrate, and 925 ml of water and separately hydrolyzed via autoclave as above. The solution was filtered as above, and the filtrate concentrated in vacuo. The residue was dissolved in c. 100 ml of hot water, and reconcentrated to a viscous oil which was treated with c. 600 ml of hot absolute ethanol. The solution was cooled to RT, at −20° C. for 72 hrs, filtered, washed with cold ethanol (2×50 ml) and ether (3×100 ml), and air/vac dried to give 118.1 g of amino acid (108.3% from 127.5 g of hydantoin). This material was dissolved in c. 150 ml of hot water, treated with c. 400 ml of hot absolute ethanol, cooled to RT then at −20° C. for 18 hrs. Filtration, absolute ethanol (−20° C., 3×50 ml) and diethyl ether (3×100 ml) washing, and air/vac drying yields 115.3 g of white, crystalline amino acid (D,L-ε-hydroxynorleucine 14).

G. DL-N-acetyl-ε-hydroxynorleucine, 16:

Five batches of D,L-N-acetyl-ε-hydroxynorleucine 16 were prepared. A 100-ml roundbottom flask equipped with a magnetic stirring bar was charged with 1.0 g (6.79 mmoles) of D,L-ε-hydroxynorleucine 14 and 25 ml of water. The solution was stirred at RT until all of the solid had dissolved at which time 1.35 g (7.45 mmoles) of p-nitrophenyl acetate and 1.9 ml (1.38 g, 13.63 mmoles) of triethylamine were added and the solution stirred at RT overnight. The mixture was acidified to pH 2.5 with 2.0N aqueous hydrochloric acid, transferred to a 250-ml separatory funnel, extracted with diethyl ether (3×25 ml), and the aqueous layer concentrated in vacuo. Acetone (50 ml) was added to the residue and after a few minutes of swirling, the solution was filtered and the solid (triethylamine hydrochloride) washed with additional acetone (2×50 ml). The filtrate was concentrated in vacuo, and the residue treated two additional times with acetone as above to yield 2.33 g of crude D,L-N-acetyl-ε-hydroxynorleucine 16.

To prepare a larger batch, a 500-ml roundbottom flask equipped with a magnetic stirring bar was charged with 10.0 g (67.94 mmoles) of D,L-ε-hydroxynorleucine and 250 ml of water. The solution was stirred at RT until all of the solid had dissolved at which time 13.54 g (74.75 mmoles) of p-nitrophenyl acetate and 19.0 ml (13.79 g, 136.31 mmoles) of triethylamine were added and the solution stirred at RT overnight. The mixture was acidified to pH 2.5 with 2.0N aqueous hydrochloric acid, transferred to a 1-L separatory funnel, extracted with diethyl ether (3×50 ml), and the aqueous layer concentrated in vacuo. Acetone (200 ml) was added to the residue and after a few minutes of swirling, the solution was filtered and the solid washed with additional acetone (2×100 ml). The filtrate was concentrated in vacuo, and the residue treated two additional times with acetone as above to yield 11.4 g of crude product.

A third 10.0 g acetylation reaction was run exactly as above to yield 13.0 g of crude D,L-N-acetyl-ε-hydroxynorleucine 16.

A 2-L roundbottom flask equipped with a magnetic stirring bar was charged with 51.7 g (0.351 moles) of D,L-ε-hydroxynorleucine and 1250 ml of water. The solution was vigorously stirred at RT until all of the solid had dissolved at which time 98.0 ml (71.15 g, 0.703 moles) of triethylamine were added. After a few minutes, 70.0 g (0.386 moles) of p-nitrophenyl acetate and 250 ml of water were added and the solution stirred at RT overnight. The mixture was acidified to pH 2.5 with 2.0 N aqueous hydrochloric acid (c. 300 ml), transferred to a 4-L separatory funnel, extracted with diethyl ether (3×150 ml), and the aqueous layer concentrated in vacuo to a white gel. Acetone (300 ml) was added to the residue and after a few minutes of swirling, the solution was filtered and the solid washed with additional acetone (2×100 ml). The filtrate was concentrated in vacuo, and the residue treated two additional times with acetone as above to yield 108.5 g of crude N-acetate. TLC/ABTAW produced two components at $R_f$ 0.50 (product) and at $R_f$ 0.34 (triethylamine hydrochloride).

A 5-L roundbottom flask equipped with a magnetic stirring bar was charged with 100.0 g (0.679 moles) of D,L-ε-hydroxynorleucine and 2.5 L of water. The solution was vigorously stirred at RT until all of the solid had dissolved at which time 190.0 ml (137.94 g, 1.363 moles) of triethylamine were added. After a few minutes, 135.4 g (0.747 moles) of p-nitrophenyl acetate and 500 ml of water were added and the solution stirred at RT overnight. The mixture was acidified to pH 2.5 with 2.0-N aqueous hydrochloric acid (c. 600 ml), transferred to a 6-L separatory funnel, extracted with diethyl ether (3×200 ml), and the aqueous layer concentrated in vacuo to a white gel. Acetone (c. 500 ml) was added to the residue and after a few minutes of swirling, the solution was filtered and the solid washed with additional acetone (2×200 ml). The filtrate was concentrated in vacuo, and the residue treated two additional times with acetone as above to yield 220.7 g of crude N-acetate.

H. L-ε-hydroxynorleucine, 14:

In order to separate out the L-isoform (or isomer) form, a 500-ml suction flask equipped with a magnetic stirring bar was charged with 13.0 g (c. 67.94 mmoles) of D,L-N-acetyl-ε-hydroxynorleucine 16 and 150 ml of water and the mixture stirred at RT until all of the solid had dissolved. The pH of the solution (initial pH, 2.25) was adjusted to 7.5 with aqueous lithium hydroxide (c. 10 ml of 2N LiOH followed by c. 2 ml of 0.1N LiOH) and 500 mg of Acylase I dissolved in 10 ml of water were filtered into the solution through a coarse sintered-glass funnel. The pH of the resulting mixture was adjusted to 7.5 and incubated at 37° C. for 18 hrs. The pH of the solution (7.2) was adjusted to 7.5 with 0.1 N LiOH, a second portion of Acylase I added as above (500 mg in 10 ml of water), and incubation at 37° C. continued for another 18 hrs. The pH of the solution was adjusted to 5.0 with glacial acetic acid, activated charcoal (500 mg) and Celite (500 mg) were added, the mixture vigorously stirred at boiling for 5 min, hot-filtered through a Buchner funnel, and the filtrate concentrated in vacuo to a viscous oil. Absolute ethanol (200 ml) was added to the oil with vigorous stirring, the mixture stirred at RT for 1 hr then at −20° C. for 30 min, filtered, washed with absolute ethanol (3×100 ml, −20° C.), and air dried to give 3.58 g of L-ε-hydroxynorleucine 14 (from 10.0 g of the D,L-amino acid). TLC/ABTAW, produced one major component at $R_f$ 0.27 and a minor (c.5%) component at $R_f$ 0.50. CHIRALPLATE (Macherey-Nagel™), solvent system—acetonitrile/methanol/water (200:50:50, v/v/v); visualization—(1) ninhydrin, heat followed by (2) 4% phosphomolybdic acid/ethanol, heat. Single component at $R_f$ 0.45 (D,L-amino acid standard gives two spots, L-isomer at $R_f$ 0.45 and the D-isomer at $R_f$ 0.38). $[2\alpha]_D+8.4°$ (conc. 2.0, 6N aq. HCl, T=23° C.), Lit[5,9]: $[\alpha]_D+22.9°$ (conc. 2.0, 6N aq. HCl).

In a second batch, a 2-L suction flask equipped with a magnetic stirring bar was charged with 108.5 g (c. 0.351 moles) of D,L-N-acetyl-ε-hydroxynorleucine 16 and 400 ml of water and the mixture stirred at RT until all of the solid had dissolved. The pH of the solution was adjusted to 7.5 with 2N aq. lithium hydroxide (c. 300 ml) and 3.5 g of Acylase I dissolved in 50 ml of water were filtered into the solution through a coarse sintered glass funnel. The pH of the resulting mixture was adjusted to 7.5 and incubated at 37° C. for 18 hrs. The pH of the solution was adjusted to 7.5 with 0.1N LiOH, a second portion of Acylase I added as above (1.5 g in 25 ml of water), and incubation at 37° C. continued for another 36 hrs. The pH of the solution was adjusted to 5.0 with glacial acetic acid, activated charcoal (2.5 g) and Celite (2.5 g) were added, the mixture vigorously stirred at boiling for 10 min, hot-filtered through a Buchner funnel, and the filtrate concentrated in vacuo to a yellow semi-solid. Absolute ethanol (800 ml) was added to the oil with vigorous stirring, the mixture stirred at reflux for 1 hr, cooled to RT then at −20° C. for 4 hrs, filtered, washed with absolute ethanol (3×100 ml, −20° C.), and air dried to give 32.0 g of L-ε-hydroxynorleucine 14 as an off-white powder. TLC/ABTAW produced one major component at $R_f$ 0.27 and a minor (c.5%) component at $R_f$ 0.50. CHIRALPLATE (Macherey-Nagel™), solvent system—acetonitrile/methanol/water (200:50:50, v/v/v); visualization—(1) ninhydrin, heat followed by (2) 4% phosphomolybdic acid/ethanol, heat. Single component at $R_f$ 0.45.

In a third batch, a 2-L suction flask equipped with a magnetic stirring bar was charged with 220.7 g (c. 0.679 moles) of D,L-N-acetyl-ε-hydroxynorleucine 16 and 800 ml of water and the mixture stirred at RT until all of the solid had dissolved. The pH of the solution was adjusted to 7.5 with 2N aq. lithium hydroxide (c. 300 ml) and 7.0 g of Acylase I dissolved in 60 ml of water were filtered into the solution through a coarse sintered glass funnel. The pH of the resulting mixture was adjusted to 7.5 and incubated at 37° C. for 72 hrs. The pH of the solution was adjusted to 7.5 with 0.1 N LiOH, a second portion of Acylase I added as above (3.0 g in 50 ml of water), and incubation at 37° C. continued for another 24 hrs. The pH of the solution was adjusted to 5.0 with glacial acetic acid, activated charcoal (5.0 g) and Celite (5.0 g) were added, the mixture vigorously stirred at boiling for 10 min, hot-filtered through a Buchner funnel, and the filtrate concentrated in vacuo to 221.4 g of a yellow semi-solid. Absolute ethanol (1.6 L) was added to the semi-solid with vigorous stirring, the mixture stirred at reflux for 1 hr, cooled to RT and stirred overnight, then at −20° C. for 4 hrs, filtered, washed with absolute ethanol (3×300 ml, −20° C.), and air dried to give 147.0 g of a moist solid.

This material was placed in a 4-L Erlenmeyer flask equipped with a magnetic stirring bar and stirred at reflux for 1 hr with 2 L of absolute ethanol. The slurry was cooled slowly overnight to RT with stirring, filtered, washed with absolute ethanol (3×300 ml), and dried (air/vac) to give 51.0 g of the L-amino acid 14. TLC; Silica Gel/ABTAW produced one major component at $R_f$ 0.27 and a minor (c.5%) component at $R_f$ 0.50. CHIRALPLATE (as above) generated a single component at $R_f$ 0.45.

I. L-N-t-Boc-ε-hydroxynorleucine, 17:

A 250-ml roundbottom flask equipped with a magnetic stirring bar was charged with 3.58 g (24.32 mmoles) of L-ε-hydroxynorleucine 14 and 120 ml of tetrahydrofuran/water (1:1, v/v). The mixture was stirred at RT until all of the solid had dissolved and 3.4 ml (2.47 g, 24.39 mmoles) of triethylamine was added. After 5 min, 6.37 g (29.18 mmoles) of di-tert-butyl dicarbonate in 10 ml of tetrahydrofuran was added and the solution stirred vigorously at RT overnight. The reaction mixture was concentrated in vacuo to remove tetrahydrofuran, and 30 ml of 1N aqueous sodium hydroxide was added. The solution was transferred to a 500-ml separatory funnel, extracted with ethyl acetate (2×25 ml), and the aqueous phase adjusted to pH 3.0 with solid citric acid. The solution was extracted with ethyl acetate (4×50ml), and the combined extracts dried over anhydrous sodium sulfate, filtered, and concentrated in vacuo to yield 1.8 g of a white solid, L- N-t-Boc-ε-hydroxynorleucine, 17. The crude product was dissolved in c. 30 ml of hot ethyl acetate and taken to the cloud point with hot hexanes. The solution was stirred and cooled to RT, then in the freezer for 2 hrs, filtered, and the solid washed with hexanes (3×10 ml) and dried (air/vac) to give 1.48 g of a white powder N-t-Boc-L-ε-hydroxynorleucine 17 (17.6% from 10.0 g of D,L-ε-hydroxynorleucine 14, 3 steps). TLC (ABTAW, as above); single component at $R_f$ 0.79. Melting point (MP) 113–114° C. (uncorrected), Lit$^{3,9}$: 112–113° C. $[\alpha]_D$−6.77° (conc. 7.0, methanol, T=23° C.), Lit$^{3,9}$: $[\alpha]_D$ −6.36+/−0.8° (conc. 7.3, methanol).

In a second batch, a 2-L roundbottom flask equipped with a magnetic stirring bar was charged with 32.0 g (0.217 moles) of L-ε-hydroxynorleucine 14 and 1 L of tetrahydrofuran/water (1:1, v/v). The mixture was stirred at RT until all of the solid had dissolved and 30.0 ml (21.78 g, 0.215 moles) of triethylamine was added. After c. 5 min, 57.0 g (0.261 moles) of di-tert-butyl dicarbonate in 100 ml of tetrahydrofuran was added and the solution stirred vigorously at RT overnight.

The reaction mixture was concentrated in vacuo to remove tetrahydrofliran, and 250 ml of 1N aqueous sodium hydroxide was added. The solution was transferred to a 4-L separatory funnel, extracted with ethyl acetate (2×100 ml), and the aqueous phase adjusted to pH 3.0 with solid citric acid (c. 200 g). The solution was shaken with 200 ml of ethyl acetate, however an emulsion formed. The solution was transferred to a 2-L Erlenmeyer flask equipped with a magnetic stirring bar and vigorously stirred with solid sodium chloride overnight at RT to salt-out the layers. The layers were separated in a 2-L separatory funnel, the aqueous phase extracted with ethyl acetate (2×200 ml), and the combined organic extracts dried overnight over anhydrous sodium sulfate. The solution was filtered and the filtrate concentrated in vacuo to yield 23.0 g of a viscous tan oil. The crude product was dissolved in 200 ml of hot ethyl acetate in a 1-L Erlenmeyer flask containing a magnetic stirring bar and taken to the cloud point with hot hexanes (c. 100 ml). The solution was stirred and cooled to RT, then in the freezer for 72 hrs, filtered, and the solid washed with hexanes (3×100 ml) and dried (air/vac) to yield 13.5 g of the L-N-t-Boc-ε-hydroxynorleucine, 17 as a white powder (31.1% from 51.7 g of D,L-ε-hydroxynorleucine, 3 steps). TLC (ABTAW, as above); one major component at $R_f$ 0.79 with a trace impurity at $R_f$ 0.85. Melting point (MP) 110–113° C. (uncorrected); $\alpha]_D$−6.41° (conc. 7.0, methanol, T=23° C.).

A third batch was made by adding 51.0 g (0.347 moles) of L-ε-hydroxynorleucine 14 and 1.6 L of tetrahydrofuran/water (1:1, v/v) in a 3-L roundbottom flask equipped with a magnetic stirring bar. The mixture was stirred at RT until all of the solid had dissolved and 50.0 ml (36.3 g, 0.357 moles) of triethylamine was added. After 10 min, 91.0 g (0.417moles) of di-tert-butyl dicarbonate in 150 ml of tetrahydrofuran was added and the solution stirred vigorously at RT overnight. The reaction mixture was concentrated in vacuo to remove tetrahydrofuran, and 500 ml of 1N aqueous sodium hydroxide was added. The solution was transferred to a 4-L separatory funnel, extracted with ethyl acetate (2×150 ml), and the aqueous phase adjusted to pH 3.0 with solid citric acid (c. 300 g). The solution was transferred to a 4-L Erlenmeyer flask equipped with a magnetic stirring bar and vigorously stirred with 300 ml of ethyl acetate overnight at RT. The layers were separated in a 4-L separatory funnel, the aqueous phase extracted with ethyl acetate (2×300 ml), and the combined organic extracts dried overnight over anhydrous sodium sulfate. The solution was filtered and the filtrate concentrated in vacuo to yield 45.6 g of a viscous tan oil. The crude product was dissolved in 200 ml of hot ethyl acetate in a 1-L Erlenmeyer flask containing a magnetic stirring bar and taken to the cloud point with hot hexanes (150 ml). The solution was stirred and cooled to RT and then placed in the freezer for 18 hours. The solution was filtered and the solid was washed with hexanes (2×100 ml) and dried (air/vac) to yield 25.4 g of an off-white powder identified as L-N-t-Boc-ε-hydroxynorleucine 17 which is the desired end product of Scheme II (FIG. 3) (30.2% from 100.0 g of D,L-ε-hydroxynorleucine 16, 3 steps). TLC (ABTAW, as above); one major component, $R_f$ 0.79 with a trace impurity at $R_f$ 0.85. Melting point (MP) 107–112° C. (uncorrected); $[\alpha]_D$ −5.44° (conc. 7.0, methanol, T=23° C.). A sample (10–20 mg) of this material was placed in a test tube and shaken with 1 ml of trifluoroacetic acid for 15 min. The sample was concentrated with a stream of nitrogen, dissolved in a few drops of water, and subjected to chiral thin-layer chromatography. CHIRALPLATE (as above) generated a single component at $R_f$ 0.45.

Figure 10:

J. O-benzyl methyl suberyl hydroxamate, 20:

O-benzylhydroxylamine hydrochloride 18 (1.44 g, 9.04 mmol) was suspended and magnetically stirred in THF (60 mL), cooled to 0° C. in an ice bath, and treated with pyridine (4.48 mL, 45.2 mmol). Methyl suberyl chloride 19 (934 mg, 4.52 mmol), dissolved in THF (8 mL), was added dropwise. The reaction mixture was stirred at 0° C. for approximately 1 h, after which time the mixture was allowed to warm to room temperature and was further stirred overnight. Ethyl acetate (80 mL) and water (50 mL) were added and the layers separated. The aqueous layer was extracted 3 times with 30 mL ethyl acetate. The combined organic layers were then washed two times with 50 mL 1N HCl, one time with 50 mL $H_2O$, and then saturated $NaHCO_3$ brine and dried (MgSO$_4$). The dried organic solution was filtered and concentrated to give 1.26 g (95%) of a clear faint yellow viscous oil identified as O-benzyl methyl suberyl hydroxamate 20. $^1$H NMR (CDCl$_3$) 1.31 (br m, 4 H), 1.62 (br m, 4 H), 2.03 (br m, 2 H), 2.29 (t, 2 H), 3.66 (s, 3 H), 4.92 (br m, 2 H), 7.38 (br s, 5 H), 8.01 (br s, 1 H); TLC (Silica Gel, Ethyl acetate/hexanes, 50:50), R$_f$ at 0.21. (O-Benzylhydroxylamine HCl R$_f$ at 0.34). See FIG. 10.

K. L-N-Boc-ε-hydroxynorleucine methyl ester, 21:

L-N-Boc-ε-hydroxynorleucine 17 from Step I above (500 mg, 2.02 mmol) was suspended and magnetically stirred in CH$_2$Cl$_2$ (4 mL) and treated with O-methyl-N,N'-diisopropylisourea (370 μL, 2.02 mmol). (The suspended material dissolved upon addition of the isourea reagent.) The reaction mixture was refluxed overnight, chilled in an ice bath (30 min), filtered on a Buchner funnel (to remove most of the N,N'-diisopropylurea) and concentrated. TLC indicated that a significant amount of starting material remained. The material was resubjected to treatment with an additional 0.5 eq O-methyl-N,N'-diisopropylisourea (184 μL, 1.01 mmol) in refluxing CH$_2$Cl$_2$ (3 mL). (Reaction solution was refluxed over the weekend, during which time the CH$_2$Cl$_2$ evaporated through the condenser leaving a viscous yellow oil and white solid stirring in the reaction flask at 50° C.; oil bath.) The concentrated reaction mixture was cooled to room temperature and CH$_2$Cl$_2$ (6 mL) was added. The resulting solution was chilled in an ice bath (30 min), filtered on a Buchner funnel (to remove most of the N,N'-diisopropylurea) and concentrated to give 642 mg crude product as a yellow oil. TLC (Silica Gel, ethyl acetate/methanol, 50:50, R$_f$ at V/V 0.74. [L-N-Boc-ε-hydroxynorleucine methyl ester 21 R$_f$ at 0.46]. This material was used directly in the next step without further purification.

L. L-N-Boc-ε-bromonorleucine methyl ester, 22:

The crude product 21 from the esterification reaction of K above (642 mg) was dissolved in THF (6 mL). Triphenylphosphine (795 mg, 3.03 mmol) was added followed by dropwise addition of carbon tetrabromide (1.005 g, 3.03 mmol) in 2 mL THF. After the mixture stirred overnight at room temperature, the THF was removed by rotary evaporation and the residue chromatographed on Silica Gel (2×30 cm), eluting with CH$_2$Cl$_2$ to yield a compound identified as the bromo-ester 22 (see FIG. 9) as a pale yellow oil: 462 mg (71% for two steps); $^1$H NMR (CDCl$_3$) 1.2–2.1 (br m, includes t-Bu singlet at 1.44, 15 H), 3.40 (t, 2 H), 3.75 (s, 3 H), 4.32 (br m, 1 H), 5.04 (d, 1 H, NH); $[\alpha]^{24}_D$ –13.3 (c. 6.41, CH$_3$OH); TLC (Silica Gel, 5:1 EtOAc/MeOH) R$_f$ at 0.74.

M. L-N-Boc-ε-bromonorleucine, 23:

L-N-Boc-ε-bromonorleucine methyl ester 22 (440 mg, 1.36 mmol) was dissolved in THF (20 mL) and treated with NaOH (55 mg in 15 mL of H$_2$O). The solution was stirred at room temperature for 2 h, and then most of the THF was removed via rotary evaporation (reaction solution was concentrated from 35 mL to approx. 15 mL). Water (15 mL) was added and the solution was extracted with Et$_2$O (1×20 mL; slight emulsion—added a small amount of brine). The aqueous layer was separated and acidified to pH 1020 2.5 via dropwise addition of 1N HCl (initial pH 11.25; total volume 1N HCL approx 2 mL). The aqueous layer was then extracted 3×20 mL EtOAc, and the combined organic layers were washed with brine. After drying (MgSO$_4$), the solution was filtered and concentrated to yield 395 mg (94%) of a clear viscous oil ((L)-N-Boc-ε-bromonorleucine, 23). TLC (Silica Gel, ethyl acetate/methanol, 5:1, v/v, R$_f$ streak from 0.19 to 0.54.

Figure 11:
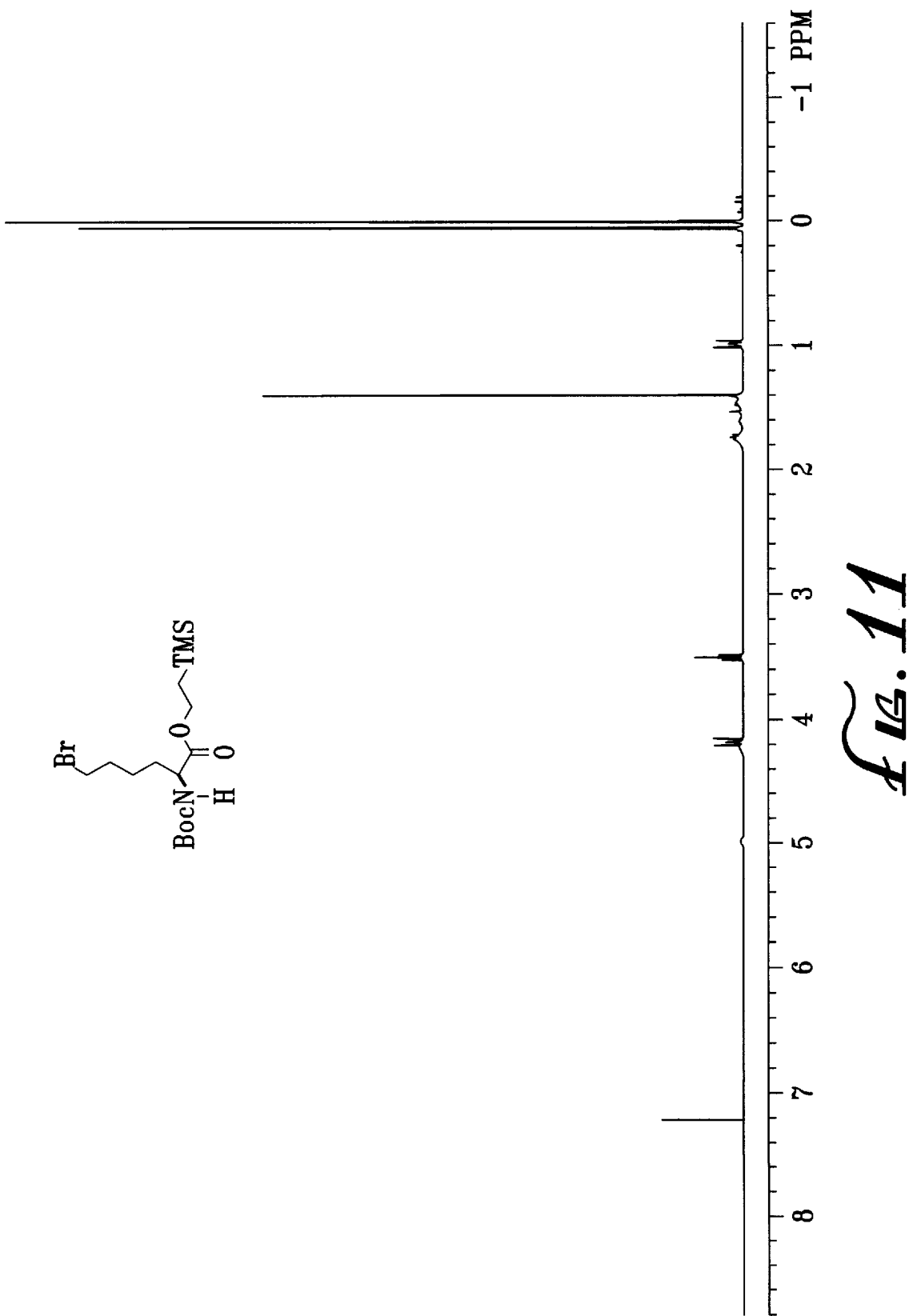

N. L-N-Boc-ε-bromonorleucine trimethylsilylethyl ester, 24:

L-N-Boc-ε-bromonorleucine 23 (225 mg, 0.725 mmol) was dissolved in CH$_3$CN (1 mL) with magnetic stirring, under argon, and cooled to 0° C. in an ice bath (15 min). Pyridine (118 μL, 1.45 mmol) and 2-(trimethylsilyl)ethanol (125 μL, 0.87 mmol) were added consecutively, dropwise via syringe. After 10 min, 1,3-dicyclohexylcarbodiimide (165 mg, 0.80 mmol) was added and a white precipitate formed after approx. 2 min. The reaction mixture was stirred for four hours at 0° C. TLC indicated that starting material was present (approx. 25% SM, 75% prod); the reaction mixture was stored at 4° C. for 72 hrs. TLC indicated the reaction had gone to completion. EtOAc (10 mL) was added, the solution stirred 5 min, filtered on a Buchner funnel to remove the white precipitate and the solid washed with EtOAc (3×10 mL). The filtrate was washed with 1N HCl, H$_2$O, saturated NaHCO$_3$, and brine (1×2 niL each), and dried (MgSO$_4$). Filtration and concentration gave approx. 350 mg of crude product which was purified by Silica Gel chromatography (2×30 cm), eluting with a gradient of 5% to 50% EtOAc/Hexanes to yield 274 mg (92%) of a pale yellow oil identified to be L-N-Boc-ε-bromonorleucine trimethylsilylethyl ester 24: $^1$H NMR (CDCl$_3$ see FIG. 11) 0.05 (s, 9 H, TMS), 1.02 (m, 2 H), 1.40–1.90 (br m, includes t-Bu singlet at 1.44, 15 H), 3.53 (t, 2 H), 4.22 (m, 2 H), 4.28 (br m, 1 H), 5.05 (br d, 1 H, NH); TLC (Silica Gel, ethyl acetate/methanol, 5:1, v/v) R$_f$ at 0.76; (Silica Gel, ethyl acetate/hexanes, 10:90, v/v) R$_f$ at 0.14. See FIG. 11.

O. L-N$^2$-Boc-N$^6$-methylsuberyl,N$^6$-(benzyloxy)lysine 2-trimethylsilylethyl ester, 25:

L-N-Boc-ε-bromonorleucine trimethylsilylethyl ester 24 from N above (270 mg, 0.658 mmol) was dissolved in 3 mL anhydrous acetone (dried over anhydrous K$_2$CO$_3$, 60+min) with magnetic stirring under argon. O-Benzylmethylsuberyl hydroxamate 20 from J above (290 mg, 0.987 mmol) was added as an acetone solution (1 mL; rinse 1×1 mL). KI (22 mg, 0.132 mmol) was added followed by anhydrous K$_2$CO$_3$ (227 mg, 1.645 mmol). The reaction mixture was heated to reflux (oil bath@65° C.) for 24 hr under argon. TLC analysis after 24 hr at reflux indicated mainly starting materials present; a new spot at R$_f$ 0.5 (Silica Gel, ethyl acetate/hexanes, 50:50, v/v) potentially desired product but faint <10%. An additional 0.3 equivalent of KI (33 mg) was added; the reaction solution was stirred vigorously at reflux under argon. TLC analysis after 96 hr at reflux indicated a darker potential product spot at R$_f$ 0.5 (reaction approximately 50% complete by TLC) so the reaction was allowed to continue at reflux. TLC after 120 hr at reflux under argon showed no significant change. The reaction solution was cooled to room temperature, filtered on a Buchner funnel (rinse 3×10 mL dry acetone) and concentrated on a rotovap. The residue was redissolved in anhydrous acetone (dried over anhydrous K$_2$CO$_3$, 5 days), KI (55 mg, 0.329 mmol) and powdered anhydrous K$_2$CO$_3$ (230 mg, 1.645 mmol) were added and the reaction mixture was stirred vigorously at reflux under argon overnight.

The reaction solution was cooled to room temperature, filtered on a Buchner funnel (rinse 3×10 mL dry acetone) and concentrated. The residue was taken up in EtOAc (20 mL) and decanted from an insoluble white solid. The EtOAc soln was concentrated to give approximately 650 mg of a clear oil. This oil was dissolved in Et$_2$O (30 mL) and washed with 0.5N NaOH (2×15 mL), H$_2$0 (15 mL), brine (15 mL), and dried (MgSO$_4$). The dried solution was filtered and concentrated to give approximately 550 mg of a clear viscous oil, which was purified by Silica Gel chromatography (2×30 cm), eluting with a gradient of 5% to 50% EtOAc/Hexanes to yield three fractions. The first fraction eluted was concentrated to yield 103 mg of a clear colorless oil which was shown by TLC (Silica Gel, 50% EtOAc/Hexanes, $R_f$ at 0.71) and $^1$H NMR to be recovered starting material, L-N-Boc-ε-bromonorleucine 2-trimethylsilylethyl ester 24.

Figure 12:
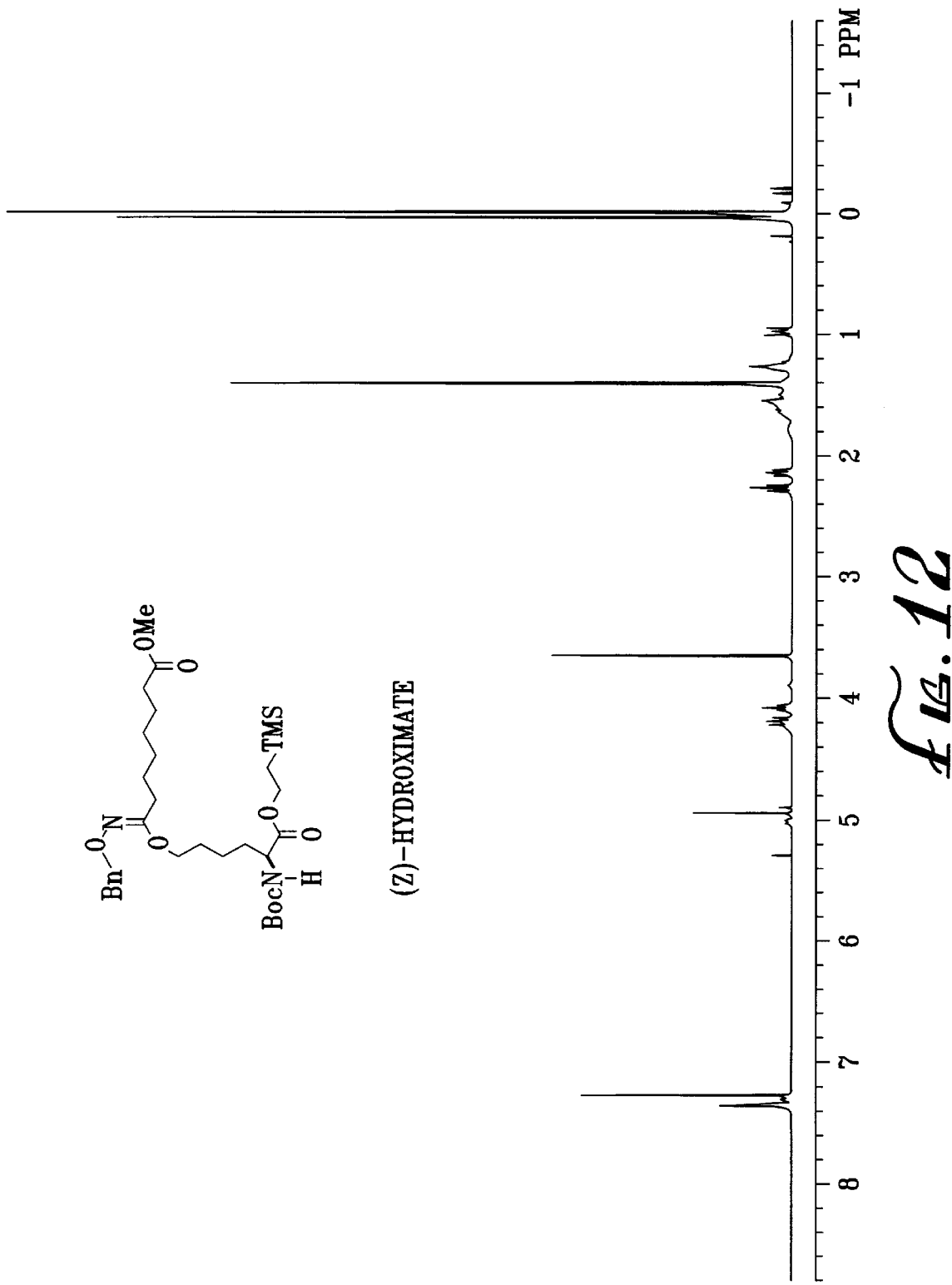

The second fraction was concentrated to give 26 mg of a clear colorless oil. TLC (Silica Gel, ethyl acetate/hexanes, 50:50, v/o) $R_f$ at 0.61. $^1$H NMR analysis indicated approximately a 9:1 mixture of, presumably, Z-hydroximate:E-hydroximate by comparison with the reported results of Maurer and Miller. Z-Hydroximate: $^1$H NMR (CDCl$_3$, see FIG. 12) 0.04 (s, 9 H, TMS), 1.01 (m, 2 H), 1.20–1.90 (br m, includes t-Bu singlet at 1.44, 23 H), 2.16 (t, 2 H), 2.29 (t, 2 H), 3.67 (s, 3 H), 4.10 (t, 2 H), 4.21 (m, 2 H), 4.24 (m, 1 H), 4.95 (s, 2 H), 5.03 (br d, 1 H, NH), 7.35 (m, 5 H).

Figure 13:
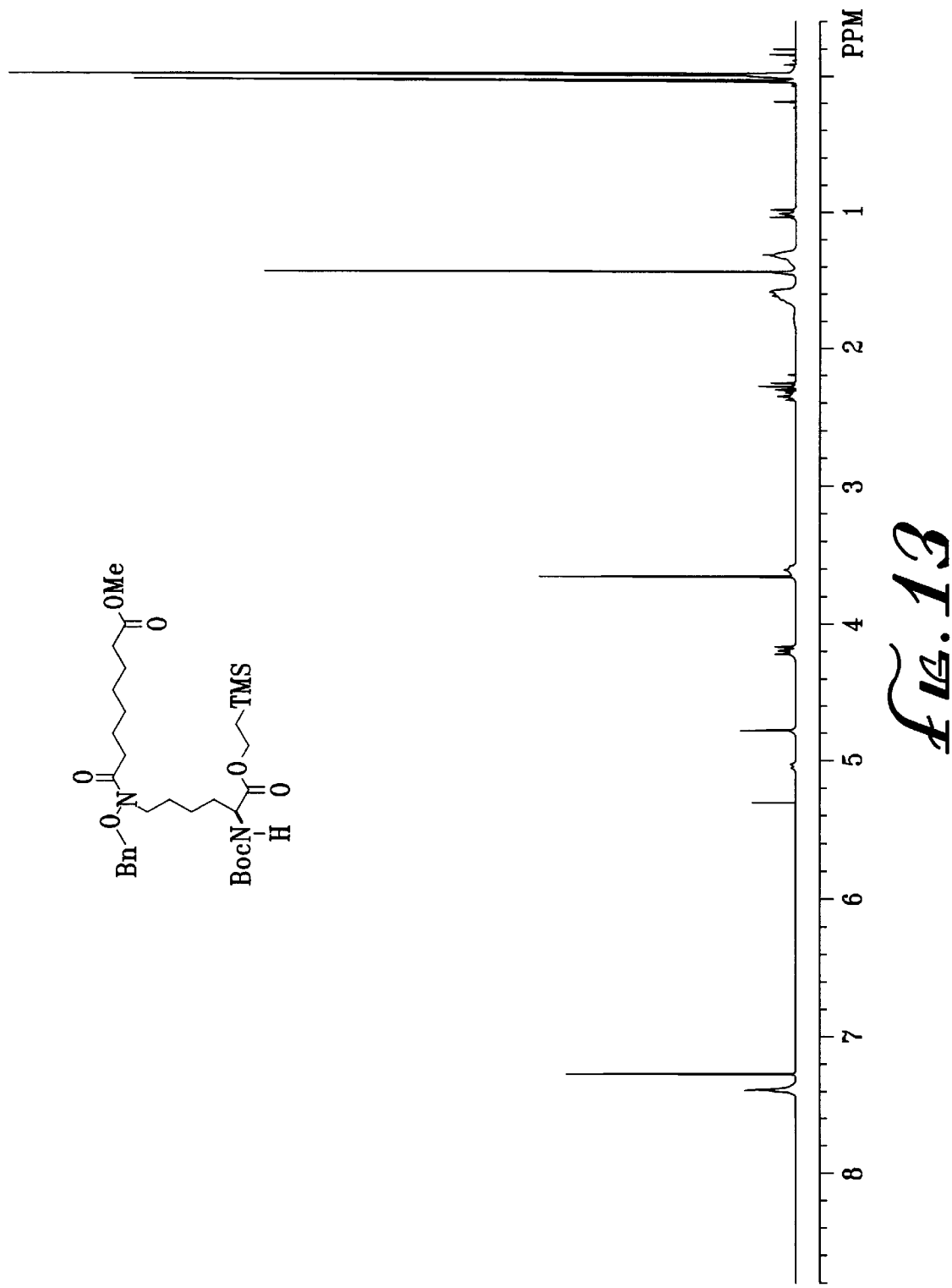

The third fraction was concentrated to give 197 mg of a clear colorless oil; $^1$H NMR analysis indicated this material to be the desired trimethylsilylethyl ester 25 product by comparison with the reported results of Maurer and Miller. Based on recovered starting material (103 mg)$^3$ the yield of the desired N-alkylated product is 78%. $^1$H NMR (CDCl$_3$, FIG. 13) 0.04 (s, 9 H, TMS), 1.00 (m, 2 H), 1.20–1.90 (br m, includes t-Bu singlet at 1.44, 23 H), 2.29 (t, 2 H), 2.36 (t, 2 H), 3.61 (br t, 2 H), 3.67 (s, 3 H), 4.20 (m, 2 H), 4.24 (m, 1 H), 4.80 (s, 2 H), 5.05 (br d, 1 H, NH), 7.38 (m, 5 H); TLC (silica gel, 50% EtOAc/Hexanes) $R_f$=0.47.

P. L-N-Boc-ε-hydroxynorleucine benzylhydroxamate, 30:

A 100 ml roundbottom flask equipped with a magnetic stirring bar and a pH probe was charged with 2.00 grams (8.09 mmoles) of L-N-Boc-ε-hydroxynorleucine 17 from Step I, 1.550 grams (9.71 mmoles) of O-benzylhydroxylamine hydrochloride, and 80 ml of water. The suspension was stirred vigorously as the pH was adjusted to 4.50 by the dropwise addition of 2N aq. sodium hydroxide resulting in the dissolution of the reactants. 1-Ethyl-3-[3-(dimethylamino)propyl]-carbodiimide hydrochloride (EDAC) (1.956 grams, 10.20 mmoles) was dissolved in 6 ml of water and added to the reaction mixture in a dropwise manner over about a 5 minute period. The solution was stirred at room temperature for 15 minutes (pH 7.26), at which time another 0.44 grams (2.30 mmoles) of the carbodiimide in 1 ml of water was added in a dropwise manner. The resulting solution was stirred for 15 minutes at room temperature (pH 7.53), transferred to a 250 ml separatory funnel, and extracted with ether (3×50 ml). The combined ether layers were extracted with 0.4N aq. sodium hydroxide (4×25 ml), the combined aqueous extracts washed with ether (1×25 ml), and acidified to pH 6.6 with citric acid. The pH dropped to 6.35 during this treatment, so 3N aq. sodium hydroxide was added dropwise to take the solution back to 6.6. The solution was extracted with dichloromethane (4×25 ml), the combined extracts dried over anhydrous magnesium sulfate, and concentrated in vacuo to give 0.88 grams (30.9% yield) of crude product. TLC analysis shows one major spot (Silica Gel; methanol/chloroform, 10:90, v/v; visualization—UV light, then anisaldehyde, heat followed by 4% phosphomolybdic acid/ethanol, heat).

A 500 ml roundbottom flask equipped with a magnetic stirring bar and a pH probe was charged with 5.00 grams (20.22 mmoles) of L-N-Boc-ε-hydroxynorleucine 17, 3.88 grams (24.31 mmoles) of O-benzylhydroxylamine hydrochloride, and 200 ml of water. The suspension was stirred vigorously as the pH was adjusted to 4.50 by the dropwise addition of 2N aq. sodium hydroxide. The solid materials had all dissolved at this point. 1-Ethyl-3-[3-(dimethylamnino)propyl]-carbodiimide hydrochloride (4.80 grams, 25.04 mmoles) was dissolved in 15 ml of water and added to the reaction mixture in a dropwise manner via a 60 ml addition funnel over about a 5 minute period. The resulting mixture was stirred at room temperature for 30 minutes before the second portion (1.10 grams, 5.74 mmoles, dissolved in 3 ml of water) was added. TLC analysis (as above) showed a substantial amount of starting material relative to product, therefore the mixture was stirred at RT overnight. The solution was transferred to a 500 ml separatory funnel and extracted with ether (3×100 ml). The combined ether layers were extracted with 0.4 N aq. sodium hydroxide (4×50 ml), and the combined aqueous extracts washed with ether (1×50 ml) and acidified to pH 6.6 with citric acid. The solution was extracted with dichloromethane (4×50 ml). The combined extracts dried over anhydrous magnesium sulfate, and concentrated in vacuo gave 2.34 grams (32.6% yield) of crude product identified as L-N-Boc-ε-hydroxynorleucine benzylhydroxamate 30. TLC analysis (as above) shows one major component.

Q. L-N-Boc-a-amino-N-(benzyloxy)caprolactam, 31:

A 50 ml roundbottom flask equipped with a magnetic stirring bar and a stopper was charged with 0.88 grams (2.50 mmoles) of L-N-Boc-ε-hydroxynorleucine benzylhydroxamate 30 from Step P, 15 ml of anhydrous tetrahydrofuran, and 0.82 grams (3.13 mmoles) of triphenylphosphine. Diethyl azodicarboxylate (DEAD) (0.52 grams, 2.986 mmoles) was added and the resulting yellow solution stirred at RT for 2 hours and checked by TLC [Silica Gel; solvent system—ethyl acetate/hexanes (30:70, v/v); visualization—(1) UV light, (2) anisaldehyde spray reagent, heat and (3) 4% phosphomolybdic acid/ethanol, heat]. The solution was concentrated in vacuo, the residue stirred with 10 ml of ethyl acetate/hexanes (30:70, v/v) and filtered through a coarse sintered glass funnel. The solid material in the funnel was washed with several portions of ethyl acetate/hexanes (4×10 ml), and the filtrate concentrated to yield 1.60 grams of crude product identified as caprolactam 31.

The preparation was repeated as follows: A 250 ml roundbottom flask equipped with a magnetic stirring bar and a stopper was charged with 2.34 grams (6.64 mmoles) of L-N-Boc-ε-hydroxynorleucine benzylhydroxamate, 50 ml of anhydrous tetrahydrofuran, and 2.18 grams (8.31 mmoles) of triphenylphosphine. Diethyl azodicarboxylate (1.45 grams, 8.33 mmoles) was added and the resulting yellow solution stirred at RT for 2 hours and checked by TLC (as above). The analysis showed the absence of starting material, therefore, the solution was concentrated in vacuo, the residue stirred with 25 ml of ethyl acetate/hexanes (30:70, v/v) and filtered through a coarse sintered glass funnel. The solid material in the funnel was washed with several portions of ethyl acetate/hexanes (4×25 ml), and the filtrate concentrated to yield 4.78 grams of crude product.

The crude cyclization reaction products from the above two preparations were combined (6.38 grams), dissolved in 5 ml of dichloromethane, injected onto a 2.5×46.0 cm glass MPLC column containing Silica Gel (230–400 mesh, grade 60), and eluted with ethyl acetate/hexanes (30:70, v/v). Fractions (50 ml) were collected, analyzed by TLC (same solvent system), pooled according to TLC results, and concentrated to give five major fractions:

| Fraction # | Weight of material | $R_f$ of component(s) | UV positive | Yield |
|---|---|---|---|---|
| 1 | 80 mg | 0.66(main), 0.73 | 0.66 | |
| 2 | 90 mg | 0.39, 0.58, 0.66 | 0.66 | |
| 3 | 190 mg | 0.37, 0.44 | 0.37 | |
| 4 | 2.22 g | 0.25(main), 0.35 | 0.25 | 72.5% |
| 5 | 281.39 mg* | 0.11*, 0.16 | 0.16 | |

*stains bright yellow with anisaldehyde reagent

A highly UV active spot, which stays at the origin in the above TLC system, was washed off the column with 100% ethyl acetate (presumably triphenylphosphine oxide).

Fraction #4 was further analyzed by HPLC [column—CAPCELL PAK C 18 (4.6×250 mm, SG120, 5 micron); solvent system—acetonitrile/water gradient (70:30 for 5 min., increase to 90:10 over 5 min., and hold for 5 min.); detection—UV@254 nm.] and shown to contain 4 major components at retention times of 3.23 min (5.05%), 4.64 min (52.22%), 5.55 min (35.43%), and 9.66 min (6.61%). The material was dissolved in 25 ml of dichloromethane and placed on a 3.0×50.0 cm bed of Silica Gel in a glass column fitted with a sintered glass frit. The sample was washed out of the flask and onto the column with additional $CH_2Cl_2$ (3×10 ml) and eluted with 100% dichloromethane. No material elutes with 1.5 L of $CH_2Cl_2$. The column was then treated with 5% ethanol in dichloromethane and 100–200 ml fractions were cut, combined according to TLC results, and concentrated in vacuo. Four major fractions were obtained:

Fraction #1: $R_f$ 0.13 spot only, 420 mg

Fraction #2: $R_f$ 0.13 (major component) and $R_f$ 0.04 spot mixture, 510 mg

Fraction #3: $R_f$ 0.13 and $R_f$ 0.04 (major component) spot mixture, 940 mg

Fraction #4: $R_f$ 0.04 spot only, 265 mg

Total material recovered from column=2.135 grams (97%)

A sample of Fraction #4 was dissolved in acetonitrile and analyzed by HPLC [column—Microsorb-MV C18 (4.6 mm×250 mm, 5 micron); method—generalmeth 70%; detector—UV @254 nm]. One major component, retention time—5.221 minutes (96.003%). This material was recrystallized from hot hexanes to give 240 mg of slightly purified material (96.7%). $^1$H NMR (CDCl$_3$) 1.20–2.10 (m, includes t-Bu singlet at 1.46, 15 H); 3.55 (m, 2 H), 4.23 (m, 1 H), 4.95 (ABq, 2 H), 5.91 (br d, 1 H), 7.30–7.46 (m, 5 H). NMR (FIG. 14) identifies this material as L-N-Boc-α-amino-N-(benzyloxy)caprolactam 31.

R. L-$N^2$-L-N-(2-benzaloxybenzoyl)-serinamidyl]-$N^6$-methylsuberyl, $N^6$-(benzyloxy)lysine 2-trimethylsilylethyl ester, 27:

According to the last step of Scheme IV (FIG. 5) L-$N^2$-Boc-$N^6$-methylsuberyl, $N^6$-(benzyloxy)lysine 2-trimethylsilylethyl ester 25 prepared in Step Q (195 mg, 0.313 mmol) was stirred with trifluoroacetic acid (TFA, 1 ml) for five minutes and then the excess TFA was removed at reduced pressure on the rotary evaporator. The residue was distributed between chloroform (2 ml) and 5% sodium carbonate (1 ml), and after vigorous stirring the layers were allowed to separate and the organic layer removed via pipet. The aqueous layer was extracted with chloroform (2×1 ml), and the combined organic layers dried briefly over $K_2CO_3$ and filtered through a Buchner funnel. The filtrate was concentrated on the rotary evaporator and the residue, identified as compound 26, FIG. 5, was dissolved in 3 ml of chloroform. According to Scheme V (FIG. 6) L-N-[2-benzyloxy (benzoyl)] serine 8 from Step D (99.0 mg, 0.313 mmol) was added to the above prepared solution of compound 26 followed by EEDQ (81.0 mg, 0.328 mmol). The sides of the roundbottom flask were rinsed with an additional 1 ml of chloroform.

The clear colorless solution became hazy approximately 15 minutes after EEDQ was added, then gradually a crystalline precipitate formed. The reaction mixture was stirred overnight at room temperature, concentrated via rotary evaporation, and the residue dissolved in 4 ml of ethyl acetate. The solution was transferred to a separatory funnel and washed with $H_2O$ (1×3 ml), 5% aq. sodium carbonate (1×3 ml), 0.2N aq. hydrochloric acid (3×3 ml), saturated aq. sodium bicarbonate bicarbonate (1×3 ml), and saturated aq. brine (1×3 ml). The solution was dried over anhydrous potassium carbonate, filtered through a Buchner funnel, and concentrated via rotary evaporation and high vacuum to leave the product as a clear colorless oil identified as L-$N^2$-[L-N-2-benzyloxy(benzoyl)-serinamidyl]-$N^6$-methylsuberyl, $N^6$-(benzyloxy)lysine 2-trimethylsilylethyl ester, 27 (185.0 mg, 72%). TLC (Silica Gel; solvent system—ethyl acetate/hexanes, 50:50, v/v) indicates a single component at $R_f$ at 0.09. TLC (Silica Gel; solvent system—ethyl acetate), $R_f$ 0.46.

Figure 15:
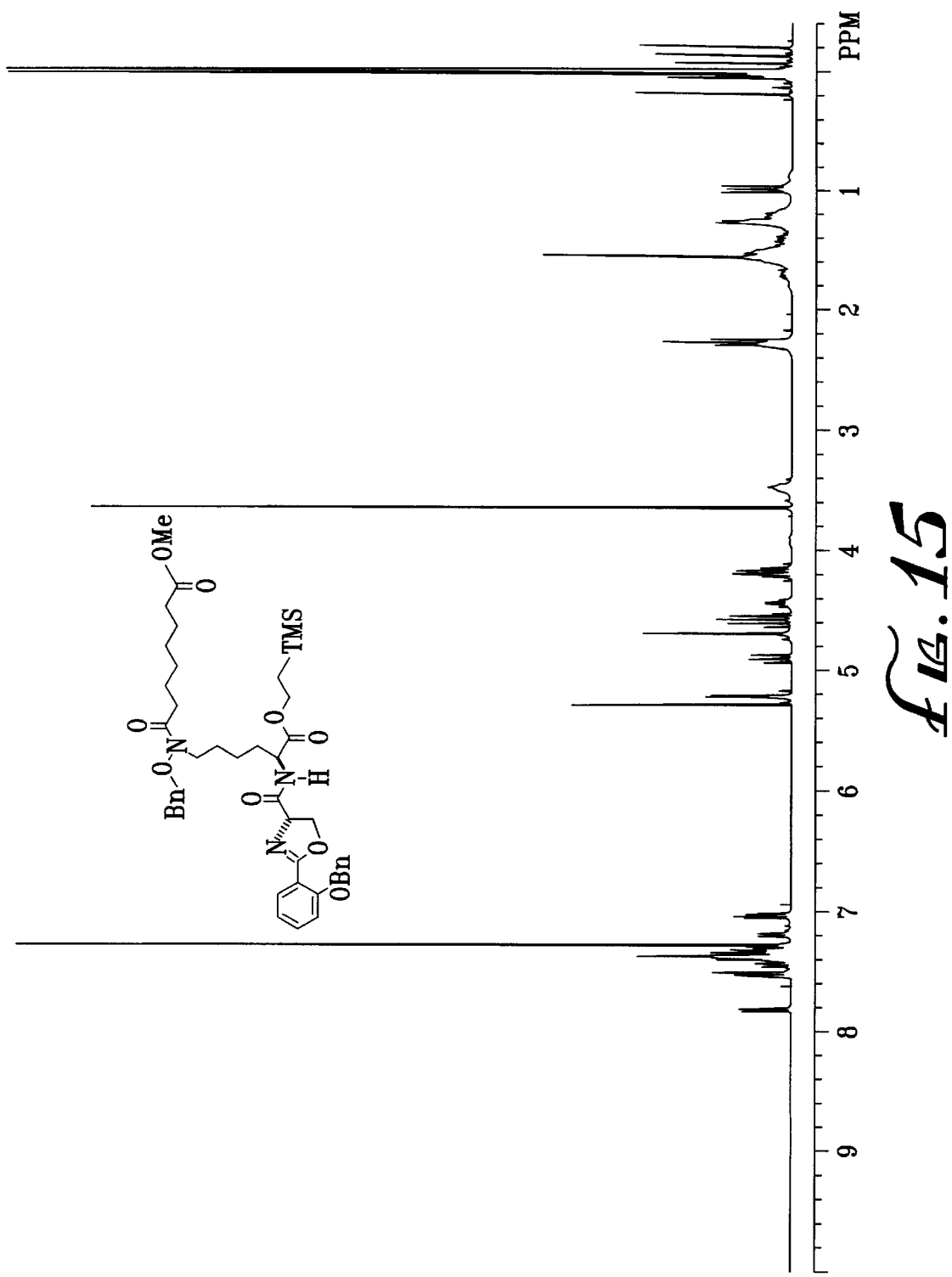
Figure 16:
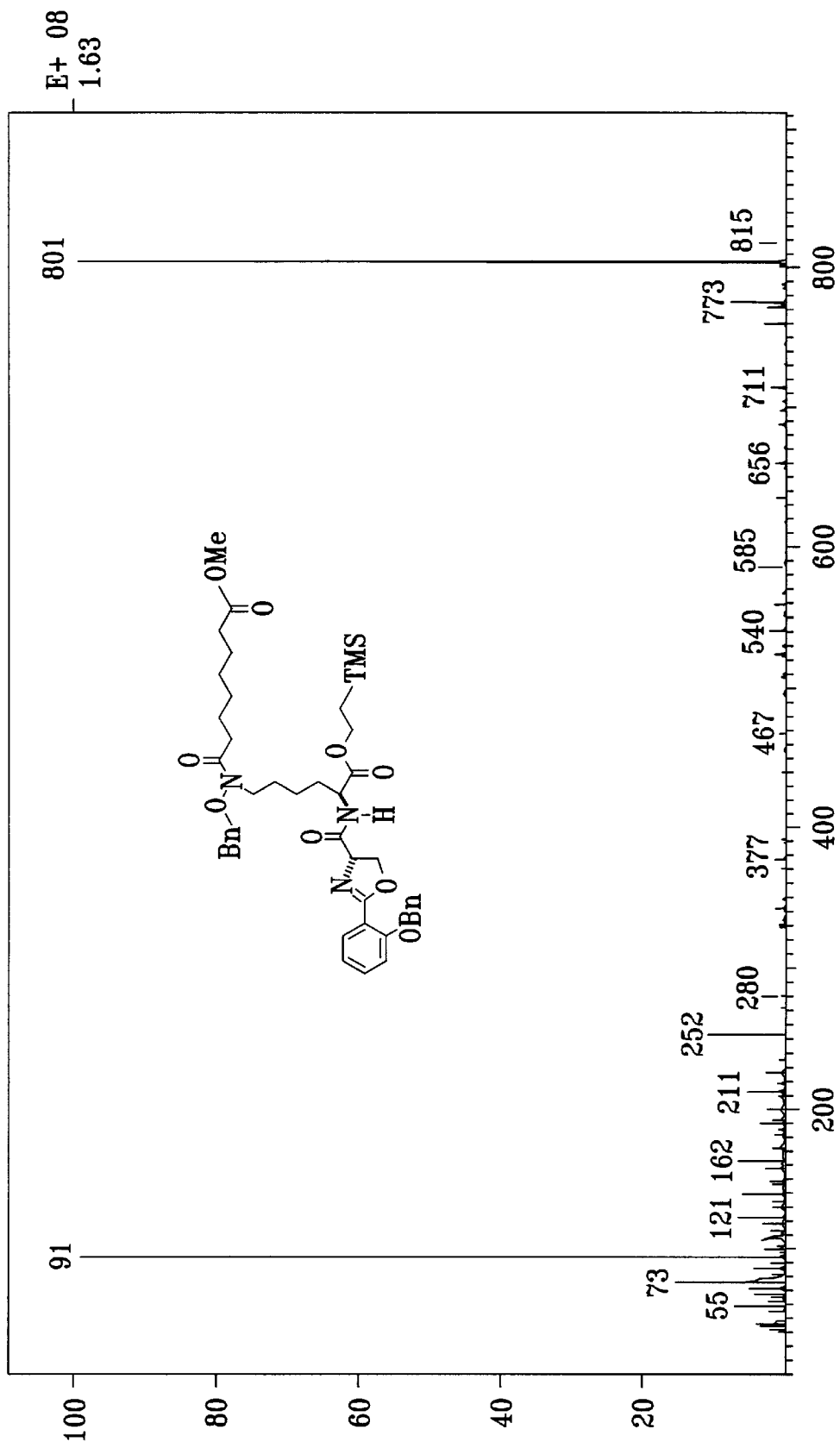

S. 2-Trimethylsilylethyl ester protected dibenzyl Exochelic acid, 28:

Crude L-$N^2$-L-N-2-benzyloxy (benzoyl) serinamidyl]-$N^6$-methylsuberyl, $N^6$-(benzyloxy)lysine 2-trimethylsilylethyl ester 27 (185 mg, 0.225 mmol) was dissolved in anhydrous tetrahydrofuran (1.5 ml, freshly distilled from calcium hydride) and the clear colorless solution chilled in an ice/salt bath (−10 to −15° C.). Thionyl chloride (115 μL, 1.579 mmol) in dry tetrahydrofuran was added to the stirred solution dropwise over 20 minutes. The reaction mixture was stored in the freezer (−20° C.) overnight. The clear yellow reaction mixture was poured into dry ether (35 ml) at −20° C. and when an expected precipitate did not form the resulting solution was poured into 50 mL dry ether at −20° C. 5% aq. Sodium bicarbonate (15 ml) was added to the cold ether solution and the mixture stirred vigorously for 15 minutes. The layers were separated, the aqueous layer extracted with ether (1×10 ml), and the combined organic layers washed with saturated aq. brine (1×10 ml). The solution was dried over anhydrous magnesium sulfate, filtered through a Buchner funnel, and the solvent removed via rotary evaporation and high vacuum to leave the crude product as a viscous orange oil 195 mg (108%). Purification by Silica Gel column chromatography (2×30 cm), eluting with a gradient of 5% to 75% ethyl acetate/hexanes yielded 100.5 mg (56%) of a clear light yellow oil identified as the protected dibenzyl Exochelic acid 28. $^1$H NMR (CDCl$_3$, FIG. 15) 0.04 (s, 9 H, TMS), 0.99 (m, 2 H), 1.10–1.80 (m, 14 H), 2.24–2.34 (m, 4 H), 3.48 (br m, 2 H), 3.66 (s, 3 H), 4.20 (m, 2 H), 4.45 (m, 1 H), 4.60 (m, 2 H), 4.71 (s, 2 H), 4.92 (dd, 1 H), 5.23 (ABq, 2 H), 6.95–7.21 (m, 3 H), 7.24–7.54 (m, 11 H), 7.78–7.84 (dd, 1 H) See Graph No. 7; Mass Spectrum (FIG. 16) m/e 91 (100, $C_7H_7^+$), 801 (99.6, $M^+$), 802 (55, M+1); TLC (Silica Gel; solvent system—ethyl acetate/hexanes, 50:50, v/v) single component at $R_f$ 0.28. TLC (Silica Gel; solvent system—ethyl acetate), $R_f$ at 0.61.

Figure 17:
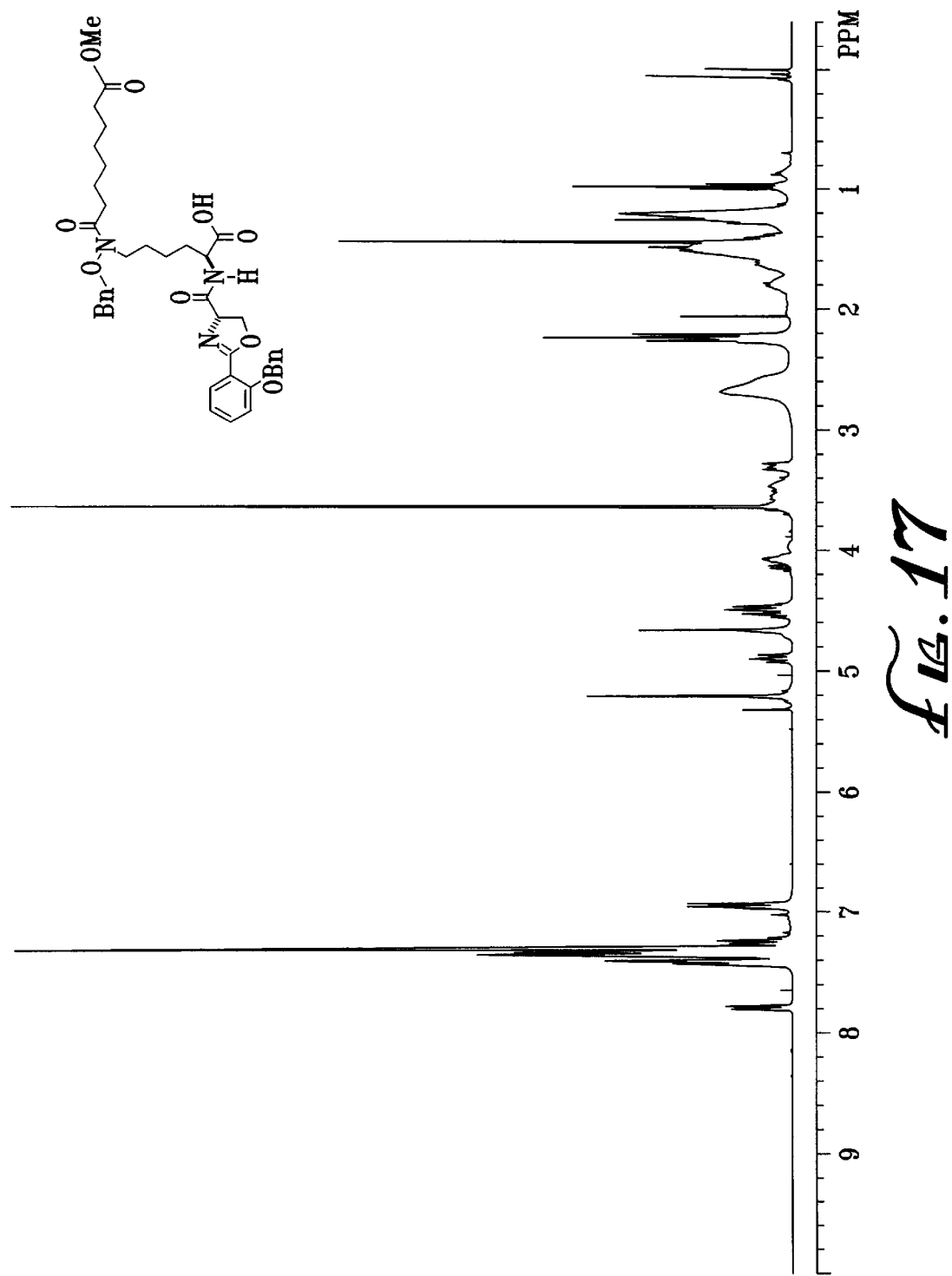

T. Dibenzyl Exochelic acid, 29:

To complete Scheme V (FIG. 6) 2-trimethylsilylethyl ester protected dibenzyl Exochelic acid 28 (8.5 mg, 0.0106 mmol) was dissolved in 0.5 ml of anhydrous tetrahydrofuran and to this solution was added tetrabutylammonium fluoride (21.2 μL 0.0212 mmol; 1M solution in tetrahydrofuran). The reaction mixture was stirred at room temperature and TLC analysis after 60 minutes at indicated that no starting material remained. The reaction solution was concentrated on the rotary evaporator, 1 ml of water added to the residue, and the aqueous solution acidified to pH 2.5 with 10 drops of 0.1N aq. hydrochloric acid. The product was extracted with ethyl acetate (3×2 ml), dried over anhydrous potassium carbonate, and filtered through a Buchner funnel. Concentration via rotary evaporator and high vacuum yielded 5.5 mg (74%) of a light tan glass idenified as the dibenzyl Exochelic acid 29. $^1$H NMR (CDCl$_3$, FIG. 17) 1.10–1.90 (m, 14 H), 2.15–2.30 (m, 4 H), 3.46 (br m, 2 H), 3.63 (s, 3 H), 4.06 (m, 1 H), 4.48 (m, 2 H), 4.65 (s, 2 H), 4.89 (dd, 1 H), 5.20 (s, 2 H), 6.87–6.95 (m, 2 H), 7.15–7.42 (m, 12 H), 7.72–7.78 (dd, 1 H); TLC (Silica Gel; solvent system—ethyl acetate/methanol, 50:50, v/v, plus 10 drops of glacial acetic acid). Single component at R$_f$ 0.67.

A large batch of the desired product was produced by dissolving the 2-trimethylsilylethyl ester protected dibenzyl Exochelic acid 28 (92.0 mg, 0.1147 mmol) in dry tetrahydrofuran (5 mL) and to this solution was added tetrabutylammonium fluoride (230 μL, 0.2294 mmol; 1M solution in tetrahydrofuran). The reaction mixture was stirred at room temperature and TLC analysis after 60 minutes indicated that no starting material remained. The reaction solution was concentrated on the rotary evaporator, 6 ml of water was added to the residue, and the aqueous solution acidified to pH 2.5 with ~10 drops of 1.0N aq. hydrochloric acid. The product was extracted with ethyl acetate (3×5 ml), dried over anh. potassium carbonate, and gravity filtered. Concentration via rotary evaporator and high vacuum yielded 52.5 mg of a light tan glass.

The crude products from the small scale (5.5 mg) and the "large" scale (52.5 mg) reactions were combined to give 58.0 mg which was purified via Silica Gel column chromatography (1×20 cm). The column was wet packed with ethyl acetate/glacial acetic acid (ratio=1 ml:1 drop, v/v), and the sample was dissolved in 2 ml of ethyl acetate. The material was eluted with ~20 mL of ethyl acetate/gl. acetic acid (ratio=1 ml:1 drop, v/v), ~50 ml of ethyl acetate/methanol (95:5, v/v)/gl. acetic acid (ratio=1 ml:1 drop, v/v), ~50 ml of ethyl acetate/methanol (90:10, v/v)/gl. acetic acid (ratio=1 ml:1 drop, v/v). Fractions were pooled and concentrated according to TLC characteristics to give 47.5 mg (54%) of the major component as a clear colorless glass. TLC (Silica Gel; solvent system—ethyl acetate/methanol (90:10, v/v)/gl. acetic acid (ratio=1 ml:1 drop, v/v); one major component at R$_f$ 0.17 and an impurity at R$_f$ 0.38.

U. S-(+)-3-hydroxybutyric acid (L-ε-hydroxybutyric acid), 33:

S-(+)-3-hydroxybutyric acid sodium salt (250 mg, 1.98 mmol) was dissolved in 2.5 ml of deionized water to give a clear colorless solution at pH 8. The stirred solution was adjusted to pH 2 by the dropwise addition of 1M aq. sulfuric acid. The solution was transferred via pipet to a continuous extraction apparatus. The free acid was obtained by continuous extraction of the acidified reaction mixture with diethyl ether overnight. The ether layer was dried over anh. magnesium sulfate, filtered, and carefully concentrated on the rotary evaporator. The product is extremely volatile, therefore the solution was concentrated for only an additional 60 seconds after all of the diethyl ether has evaporated to yield 201 mg (98%) of a clear colorless oil. This material was used directly in the next step without further purification.

Benzyl epi-cobactin, 34:

L-N-Boc-α-amino-N-(benzyloxy)caprolactam 31 (240 mg, 0.718 mmol) was stirred at room temperature for five minutes with 1 ml of trifluoroacetic acid. The trifluoroacetic acid was removed at reduced pressure on the rotovap and the residue distributed between 5 ml of dichloromethane and 5 ml of 1N aq. ammonium. The aqueous layer was extracted with dichloromethane (2×5 ml), the combined extracts were dried over anhydrous potassium carbonate, filtered, and concentrated to leave 188 mg (110%) of an oil 32. This material was used directly in the next step without further purification. The residue was stirred in 2 ml of dry tetrahydrofuran (freshly distilled from calcium hydride) to give a clear colorless solution with an insoluble film. The above prepared L-ε-hydroxybutyric acid 33 (88 mg, 0.843 mmol) dissolved in 2 ml of dry tetrahydrofuran was added to the stirred solution and a white precipitate formed. 2-Ethoxy-N-(ethoxycarbonyl)-1,2-dihydroquinoline (EEDQ, 240 mg, 0.962 mmol) was added, the reaction mixture stirred and heated at 50° C. overnight, cooled to room temperature, and concentrated via rotovap to 461 mg of a white solid. The crude product was purified by recrystallization from ethyl acetate/ether to give 180 mg (78.25%) of a white powder identified as benzyl epi-cobactin 34.

$^1$H NMR (CDCl$_3$, FIG. 18) 1.24 (d, 3 H), 1.30–2.05 (m, 6 H), 2.27–2.44 (m, 2 H), 3.44–3.68 (m, 2 H), 4.19 (m, 1 H), 4.47 (m, 1 H), 4.95 (ABq, 2 H), 6.93 (br d, 1 H), 7.32 –7.46 (m, 5 H); TLC (Silica Gel, ethyl acetate/methanol, 5:1, v/v) R$_f$ at 0.49; Melting point: 138–139° C. (uncorrected).

W. Tribenzyl Exochelin 786SM(R), 35:

Dibenzyl Exochelic acid 29 from Step T (47.0 mg, 0.0669 mmol) was dissolved in 1 ml of dry tetrahydrofuran. Benzyl epi-cobactin 34 from Step V (21.5 mg, 0.0669 mmol) and triphenylphosphine (26.4 mg, 0.1005 mmol) were added and the mixture stirred at room temperature until all the material had dissolved. Diethyl azodicarboxylate (15.83 μL 0.1005 mmol) was added via syringe to the stirred solution and after one hour at room temperature TLC analysis indicated a new spot (presumably product), along with a strong spot for dibenzyl exochelic acid (roughly 60% product/40% starting material) and faint spot for benzyl epi-cobactin. TLC analysis after two hours gave similar results, therefore, an additional 0.25 equivalents of benzyl epi-cobactin (5.4 mg), 0.5 equivalents triphenylphosphine (8.8 mg), and 0.5 equivalents of diethyl azodicarboxylate (5.3 L) were added. TLC analysis after an additional 1.5 hours indicated a somewhat improved product/dibenzyl exochelic acid ratio (roughly 80% product/20% starting material), although the spot corresponding to dibenzyl exochelic acid remained strong. TLC analysis after 3 hours indicated that the reaction mixture has remained unchanged. Again, an additional 0.25 equivalents of benzyl epi-cobactin (5.4 mg), 0.5 equivalents of triphenylphosphine (8.8 mg), and 0.5 equivalent diethyl azodicarboxylate (5.3 L) were added. TLC analysis one hour later indicated again an improved product/dibenzyl exochelic acid ratio (roughly 90% product/10% starting material). At this point, the reaction flask was capped tightly and stored at 34° C. for 48 hours.

Figure 19:
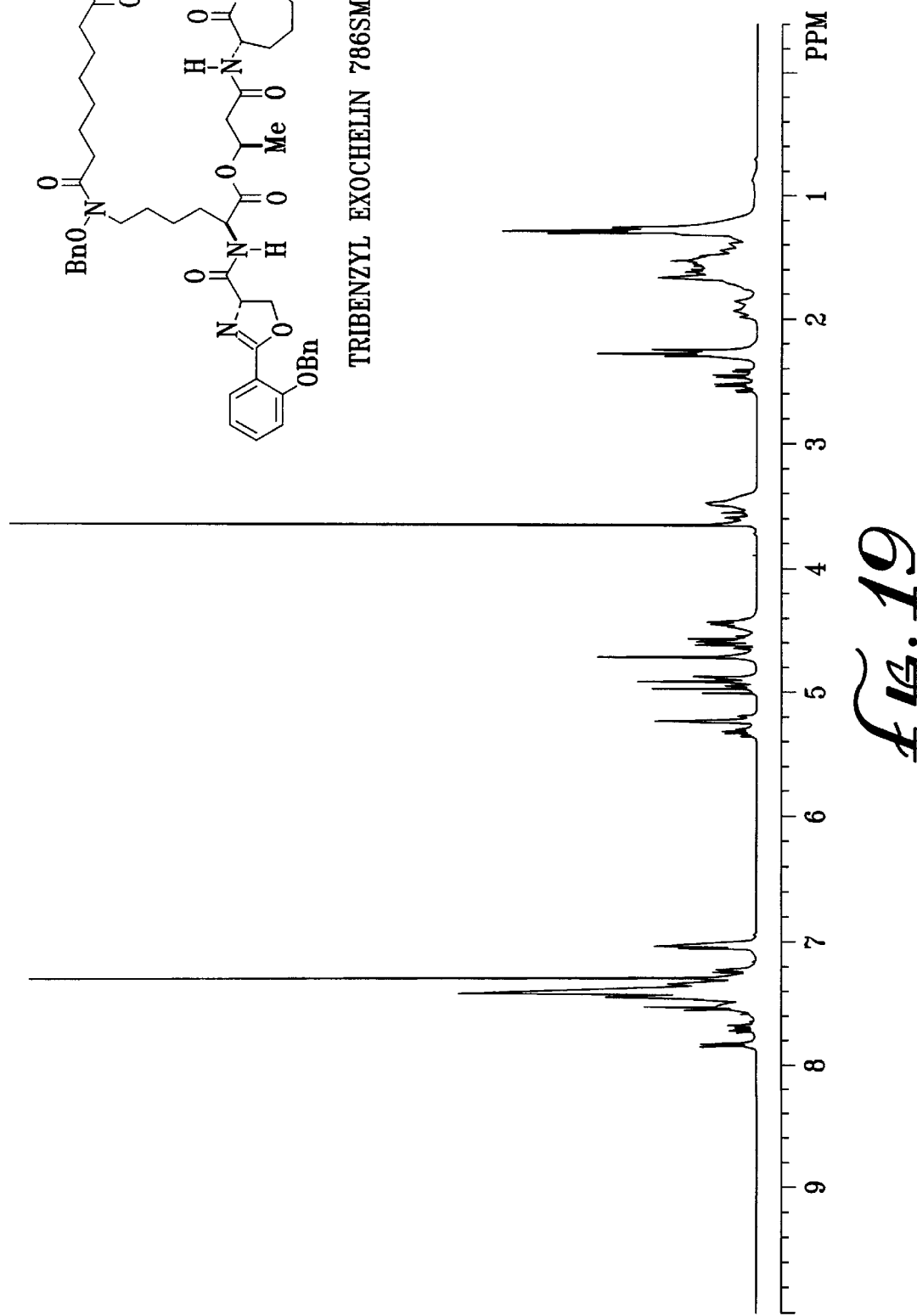

TLC analysis indicated no significant changes occurred; therefore, the solvent was removed on the rotovap to leave a yellow oil. This material was purified by Silica Gel chromatography (1×20 cm). The column was wet packed with ethyl acetate/hexanes (50:50, v/v) and the crude product dissolved in 2 ml of ethyl acetate/hexanes (50:50, v/v) and loaded onto the column. The material was eluted with 50 ml of ethyl acetate/hexanes (50:50, v/v), 25 ml of ethyl acetate/hexanes (75:25, v/v), 25 ml of ethyl acetate, 100 ml of ethyl acetate, and finally ethyl acetate/methanol (90:10, v/v). Fractions (5–10 ml) were collected, pooled, and concentrated according to TLC characteristics. TLC analysis of the major pooled fraction indicated that the product was slightly contaminated with both a slightly higher $R_f$ faint streak and benzyl epi-cobactin at lower $R_f$. A second purification by preparative TLC (Silica Gel GF, 20×20 cm, 2000 microns) developing with ethyl acetate/methanol (95:5, v/v), followed by product isolation gave 41.1 mg (61.2%) of a clear colorless glass identified as tribenzyl Exochelin 35. $^1$H NMR (CDCl$_3$, FIG. 19) 1.10–2.00 (m, includes 3 H d at 1.29, 23 H), 2.20–2.34 (m, 4 H), 2.50 (m, 2 H), 3.40–3.67 (m, includes 3 H s at 3.65, 7 H), 4.38–4.50 (m, 2 H), 4.58 (m, 2 H), 4.70 (br s, 2 H), 4.91 (m, 1 H), 4.93 (ABq, 2 H), 5.23 (ABq, 2 H), 5.32 (m, 1 H), 6.96–7.04 (m, 3 H), 7.17–7.72 (m, 17 H), 7.81 (dd, 1 H); Mass Spectrum (FAB) m/e 91 (100, C$_7$H$_7^+$), 1004 (50, M+1); TLC (Silica Gel, ethyl acetate/methanol, 5:1, v/v, $R_f$ at 0.70.

X. Exochelin 786SM(R), 1:

Tribenzyl Exochelin 786SM(R) 35 (39.0 mg, 0.0388 mmol) was dissolved in 2 ml of isopropanol. A solution of 10% palladium on carbon (20.0 mg) in 1 ml of isopropanol was added via pipet and the resulting solution stirred for 6 hours under hydrogen (1 atm, balloon) at room temperature. The solution was filtered through a small Buchner funnel and concentrated to give 27.5 mg (96.6%) of a clear colorless glass. TLC analysis (Silica Gel; solvent system—ethyl acetate/methanol/gl. acetic acid, 5:1:5, v/w) indicated that no tribenzyl starting material ($R_f$ 0.73) was present. The main spot, presumably the desired product ($R_f$ 0.54), was contaminated with very small amounts of two slightly less polar materials, presumably the monobenzylated Exochelin ($R_f$ 0.59), and the dibenzylated Exochelin ($R_f$ 0.64). HPLC analysis showed three peaks at 3.29 min (93%), 6.54 min (6%), and 9.58 min (1%), presumably corresponding to Exochelin, monobenzylated, and dibenzylated materials, respectively. The crude product was redissolved in 1.5 ml of isopropanol and treated with a solution of 15 mg 10% palladium on carbon in 1 ml of isopropanol.

Figure 20:
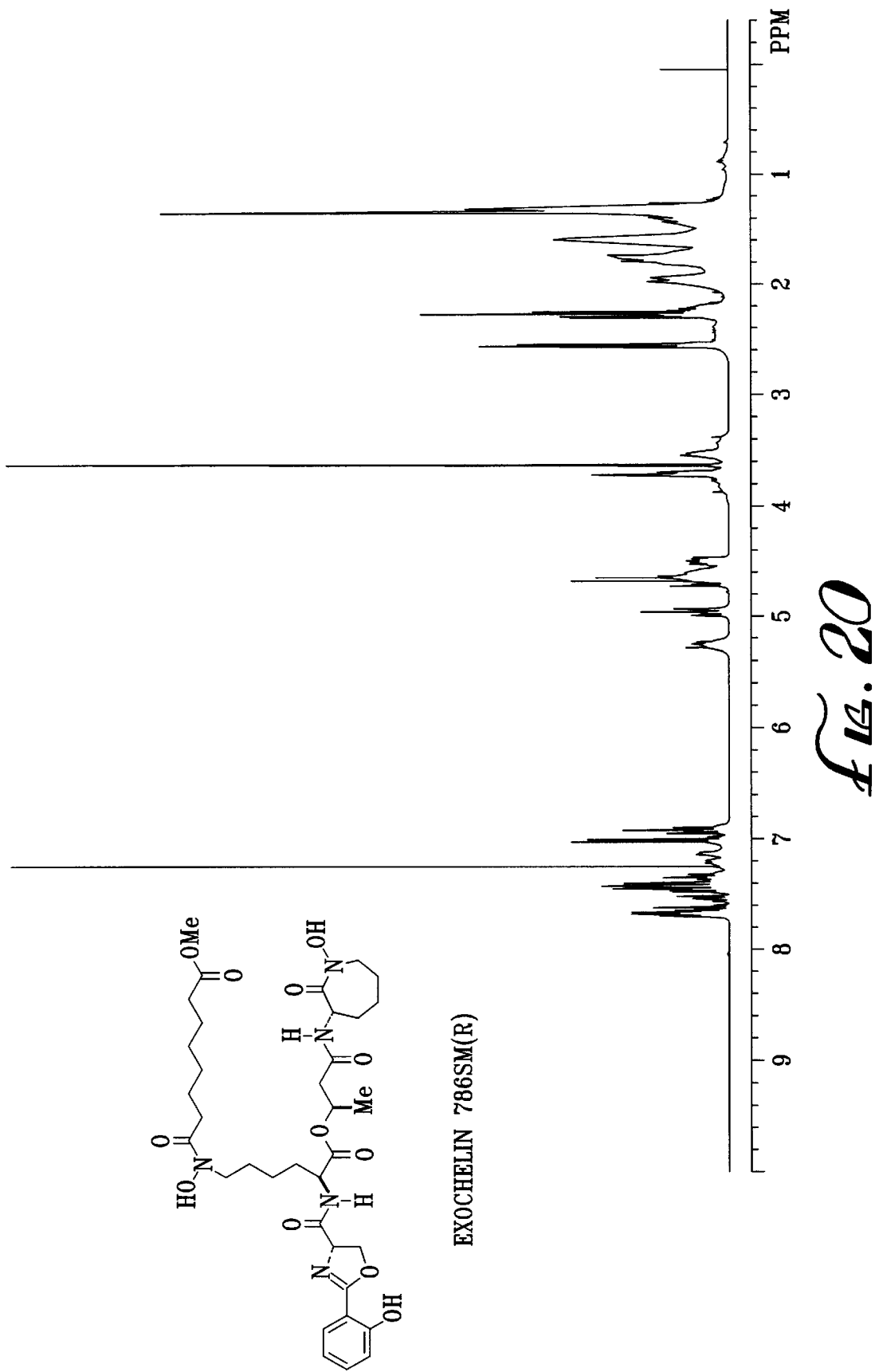
Figure 21:
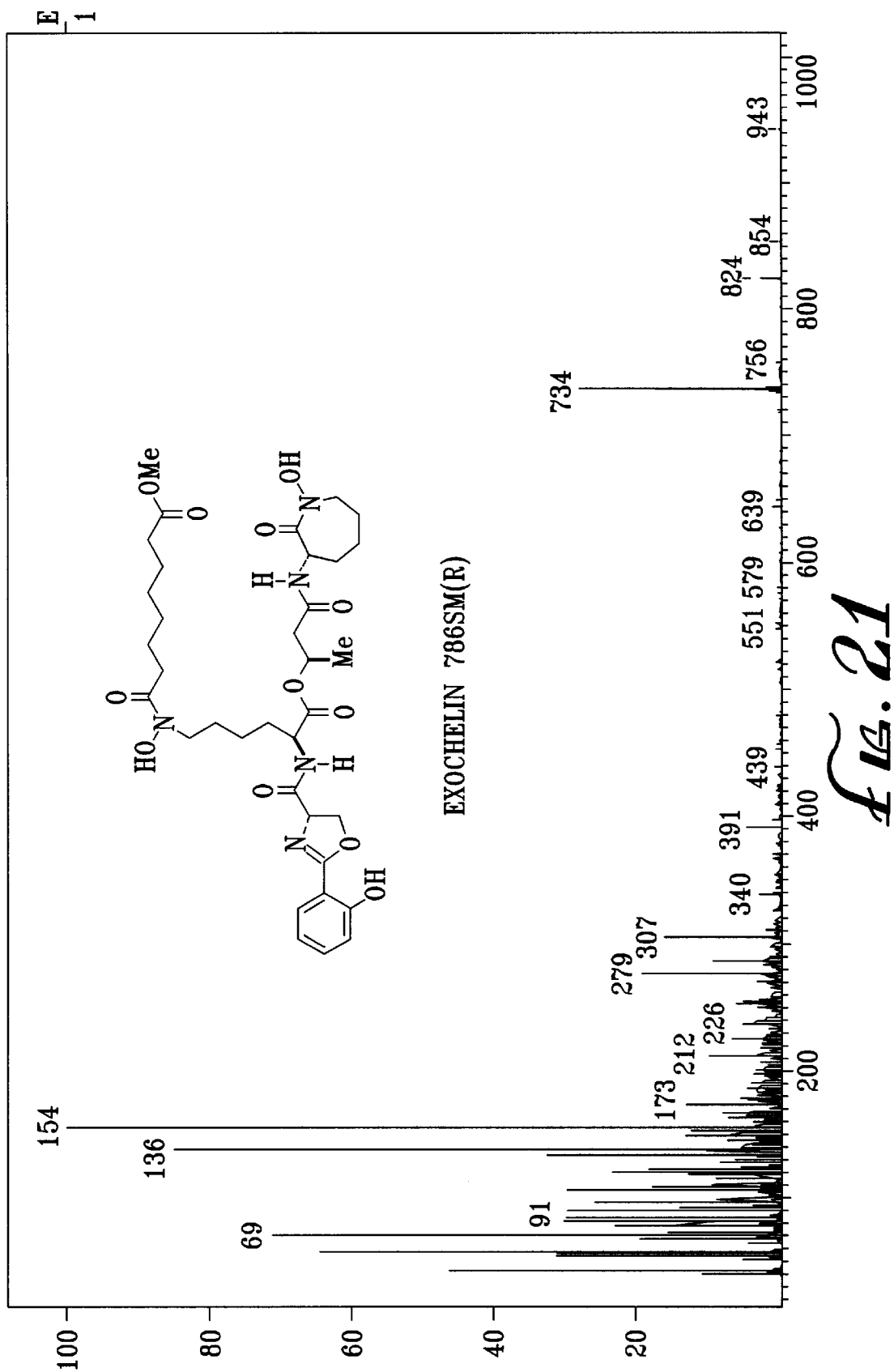

The resulting solution was stirred at room temperature under 1 atm hydrogen for four hours. The solution was filtered through a small Buchner funnel followed by filtration through a 2 micron filter disk. Concentration gave 24.8 mg (87.1%) of a clear colorless glass. TLC analysis indicated that the material had been completely and cleanly converted to one spot at $R_f$ 0.53, identified to be the desired product Exochelin 786 SM(R)1. $^1$H NMR (CDCl$_3$, FIG. 20)1.20–2.10 (m, includes 3 H d at 1.35, 23 H), 2.18–2.35 (m, 4 H), 2.58 (m, 2 H), 3.56 (m, 2 H), 3.66 (s, 3 H), 3.75 (m, 2 H), 4.46–4.76 (m, 4 H), 4.98 (M, 1 H), 5.27 (m, 1 H), 6.88–7.74 (m, 6 H). Mass Spectrum (FAB, FIG. 21) m/e 734 (30, M+1); TLC (silica gel, 5:1:1 EtOAc/MeOH/HOAc) $R_f$ at 0.53.

Having described preferred embodiments of the invention with reference to the accompanying figures, it is to be understood that the invention is not limited to those precise embodiments, and that various changes and modifications may be effected therein by one skilled in the art without departing from the scope or spirit of the invention as defined in the appended claims.

As set forth in U.S. Pat. No. 5,721,209 the Exochelins are a family of compounds which differ from each other by the number of CH$_2$ groups in the alkyl side chain of the F functional unit, referred to as the R side chain in the '209 patent, or the absence or presence of a double bond in said side chain which will hydrogenate during the final step of this sequence. Additionally, the serine and theronine series relate to the presence or absence of methyl group (i.e. Horchs) at R$_3$ as shown in '209, which corresponds to the available carbon in the 5 member ring of the D portion. One skilled in the art would recognize the modifications to the above synthesis, particularly by using a different compound in Scheme III (FIG. 4) in place of methyl suberyl chloride 19 in forming F and/or L-threonine in place of L-Serine in Scheme I (FIG. 2) in forming the D component. In particular, methyl suberyl chloride 19 can be formed from the dicarboxylic acid suberic acid (octanedioic acid, COOH (CH$_2$)$_6$ COOH). Modifying, shortening or enlarging the (CH$_2$)$_6$ group in the starting dicarboxylic acid and using the appropriate methylated and chlorinated form in the above reaction scheme will result in a different member of the Exochelin family. Alternative starting materials are oxalic, malonic, succinic, glutaric, adipic, pimelic, azelaic, sebacic, maleic, and fumaric acid and branched or substituted variations thereof. One skilled in the art would recognize the numerous homologous dicarboxylic acids which could be used. By the above, it is not suggested that C$_{10}$ dicarboxylic acid is the largest usable reactant. For example if undeconoic acid was used in place of suberic acid the Exochelin 828 SM(R)would result, and use of L-threonine in place of serine in the same preparation would produce Exochelin 842 TM(R). Likewise dodecanoic acid would result in Exochelin 842 SM(R)

Accordingly, no limitation on the scope or spirit of the appended claims is intended by the descriptions of the preferred versions of applicants' processes and products as defined hereinafter.

What is claimed is:

1. A process for the synthesis of Exochelin 786SM(R) comprising the steps of:

generating N-(2-benzyloxy-benzoyl)-L-serine;

creating N-t-Boc-L-ε-hydroxynorleucine and reacting same to produce L-N-Boc-ε-bromonorleucine trimethylsilylethyl ester;

coupling O-benzyl methyl suberyl hydroxamate with the L-N-Boc-ε-bromonorleucine trimethylsilylethyl ester to give L-N$^2$-Boc-N$^6$-methylsuberyl, N$^6$-(benzyloxy) lysine 2-trimethylsilylethyl ester;

removing the N-tert-butoxycarbonyl protecting group of L-N$^2$-Boc-N$^6$-methylsuberyl, N$^6$-(benzyloxy) lysine 2-trimethylsilylethyl ester to yield a substituted lysine, and coupling the same with the L- N-[2-benzyloxy-(benzoyl)]serine to yield a 2-trimethyl silylethyl ester of dibenzyl Exochelic acid;

transforming the 2-trimethyl silylethyl ester of dibenzyl Exochelic acid to dibenzyl Exochelic acid;

preparing benzyl epi-cobactin;

forming an ester bond between dibenzyl Exochelic acid and benzyl epi-cobactin to form an intermediate; and, hydrogenolytically removing three benzyl groups from said intermediate, resulting in the synthesized Exochelin 786SM(R).

2. The process according to claim 1, wherein said step of generating N-(2-benzyloxy-benzoyl)-L-serine comprises the steps of:

protecting of salicylic acid, making benzyl-2-benzyloxybenzoate using benzyl chloride and anhydrous potassium carbonate in refluxing N,N-dimethylformamide to form a crude product;

hydrolyzing said crude product with methanolic sodium hydroxide yielding 2-benzyloxybenzoic acid;

reacting 2-benzyloxybenzoic acid with p-nitrophenol and dicyclohexylcarbodiimide in ethyl alcohol to produce 4-nitrophenyl-2-(benzyloxy) benzoate; and, treating 4-nitrophenyl-2-(benzyloxy)benzoate with L-serine and triethylamine in tetrahydrofuran in water.

3. The process according to claim 1, further including the step of preparing L-ε-hydroxynorleucine for conversion to N-t-Boc-L-ε hydroxy-norleucine comprising:

aqueously hydrolyzing 3,4-dihydro-2H-pyran with hydrochloric acid acting as a catalyst;

treating a resultant intermediate aldehyde with sodium bisulfite to form a bisulfite addition product;

treating the bisulfite addition product with potassium cyanide in situ to generate cyanohydrin;

cyclizing the cyanohydrin using ammonium carbonate to produce hydatoin and dihydropyran;

hydrolyzing the hydantoin in an autoclave with aqueous barium hydroxide to yield D,L-ε-hydroxynorleucine;

acetylating the D, L compound to yield an L-isomer by way of enzymatic resolution; and protecting said L-isomer.

4. The process according to claim 3, wherein said step of creating N-t-Boc-L-ε-hydroxynorleucine further comprises:

treating L-ε-hydroxynorleucine with di-tert-butyl dicarbonate and triethylamine in tetrahydrofuran and water to block the N-terminus of the amino acid.

5. The process according to claim 1, wherein said step of generating O-benzyl methyl suberyl hydroxamate comprises:

reacting O-benzylhydroxylamine hydrochloride with methyl suberyl chloride in THF in the presence of excess pyridine.

6. The process according to claim 1, further including reacting the N-t-Boc-L-ε-hydroxynorleucine with O-methyl-N,N diisopropylisoruea yielding a methyl ester;

converting the methyl ester into a corresponding acid;

reacting said corresponding acid with 2-(trimethylsilyl) ethanol in the presence of 1,3-dicyclohexylcarbodiimide and pyridine in acetonitrile to form L-N-Boc-ε-bromonorleucine trimethylsilylethyl ester.

7. The process of claim 1 wherein the step of forming the dibenzyl Exochelic acid by reacting the L-N-[2-benzyloxy-(benzoyl)]-L-serine with the substituted lysine first produces L-N$^2$-[L-N-2-benzyloxy(benzoyl)serinamidyl]-N$^6$-methylsuberyl, N$^6$-(benzyloxy)lysine 2-trimethylsilylethyl ester which was exposed to thionyl chloride in tetrahydrofuran to to form a 2-trimethylsilylethyl ester protected dibenzyl Exochelic acid, said 2-trimethylsilylethyl ester being stripped from the protected compound by exposure to tetrabutylammonium fluoride.

8. The process according to claim 1, wherein said step of transforming the L-N-Boc-ε-bromonorleucine trimethylsilylethyl ester to dibenzyl Exochelic acid further comprises:

providing an appropriately protected ester and a hydroxamate;

reacting said appropriately protected ester with said hydroxamate in the presence of potassium iodine and anhydrous potassium carbonate in refluxing acetone overnight;

adding additional potassium iodide, vigorously mixing and refluxing over 12 hours;

filtering, concentrating and chromatographically purifying a plurality of fractions from a resulting mixture;

separating a desired N-alkylated product;

coupling said desired N-alkylated product with L-N-[2-benzyloxy (benzoyl)]-L-serine using 2-ethoxy-N-(ethoxycarbonyl)-1,2-dihydroquinoline in chloroform;

dehydrative cyclization by treatment with thionyl chloride to produce oxazoline;

transforming oxazoline to dibenzyl Exochelic acid by selective removal of the 2-trimethylsilylethyl ester; and, treating a tetrahydrofuran solution of 2-trimethylsilylethyl ester of dibenzyl Exochelic acid with two equivalents of tetrabutylammonium fluoride.

9. The process according to claim 1, wherein said step of preparing benzyl epi-cobactin further comprises:

reacting L-N-Boc-ε-norleucine with O-benzylhydroxylamine in aqueous solution at pH 4.5 using 1-ethyl-3-(diethylamino) propyl carbodiimide hydrochloride as a coupling agent to form L-N-Boc-ε-hydroxynorleucine benzylhydroxamate;

treating the benzylhydroxamate with triphenylphosphine and diethyl azodicarboxylate in anhydrous tetrehyrdofuran to induce cyclization to caprolactam;

removing the N-tert-butoxycarbonyl (N-t-Boc) protecting group by treatment with trifluoroacetic acid to form the free amine, and reacting said free amine with hydroxybutyric acid in the presence of EEDQ in THF.

10. The process according to claim 1, wherein said step of reacting the dibenzyl Exochelic acid with the benzyl epi-cobactin to form an intermediate further comprises:

mixing said compounds in the presence of a triphenyphosphine/DEAD; and isolating tribenzyl Exochelin 786SM(R).

11. A process for the synthesis of an Exolchelin comprising the steps of:

generating N-[2-benzyloxy-(benzoyl)]-L-serine;

creating N-t-Boc-L-ε-hydroxynorleucine and reacting same to produce L-N-Boc-ε-bromonorleucine trimethylsilylethyl ester;

providing a dicarboxylic acid and forming an O-benzyl methyl hydroxamate from the dicarboxylic acid;

coupling the O-benzyl methyl hydroxamate with the L-N-Boc-ε-bromonorleucine trimethylsilylethyl ester to give an L-N$^2$-Boc-N$^6$-methyl, N$^6$-(benzyloxy)lysine 2-trimethylsilylethyl ester which incorporates the dicarboxylic acid as modified above;

removing the N-tert-butoxycarbonyl protecting group from the L-N$^2$-Boc-N$^6$-methyl, N$^6$-(benzyloxy) lysine 2-trimethylsilylethyl ester to yield a substituted lysine, and coupling the same with the L-N [2-benzyloxy (benzoyl)]serine to yield a 2-trimethyl silylethyl ester of dibenzyl Exochelic acid;

transforming the 2-trimethyl silylethyl ester of dibenzyl Exochelic acid to dibenzyl Exochelic acid;

preparing benzyl epi-cobactin;

forming an ester bond between the dibenzyl Exochelic acid and benzyl epi-cobactin to form an intermediate, and hydrogenolytically removing three benzyl groups from said intermediate, resulting in the synthesized Exochelin.

12. A process for the synthesis of an Exolchelin comprising the steps of:

generating N-[2-benzyloxy (benzoyl)]-L-threonine;

creating L-N-t-Boc-ε-hydroxynorleucine and reacting same to produce L-N-Boc-ε-bromonorleucine trimethylsilylethyl ester;

providing a dicarboxylic acid and forming an O-benzyl methyl hydroxamate from the dicarboxylic acid;

coupling the O-benzyl methyl hydroxamate with the L-N-Boc-ε-bromonorleucine trimethylsilylethyl ester to give an L-$N^2$-Boc-$N^6$-methyl, $N^6$-(benzyloxy)lysine 2-trimethylsilylethyl ester which incorporates the dicarboxylic acid as modified above;

removing the N-tert-butoxycarbonyl protecting group from the L-$N^2$-Boc-$N^6$-methyl, $N^6$-(benzyloxy)lysine 2-trimethylsilylethyl ester to yield a substituted lysine, and coupling the same with the L-N-[2-benzyloxy (benzoyl)]threonine to yield a 2-trimethyl silylethyl ester of dibenzyl Exochelic acid;

transforming the 2-trimethyl silylethyl ester of dibenzyl Exochelic acid to dibenzyl Exochelic acid;

preparing benzyl epi-cobactin;

forming an ester bond between the dibenzyl Exochelic acid and benzyl epi-cobactin to form an intermediate, and hydrogenolytically removing three benzyl groups from said intermediate, resulting in the synthesized Exochelin.

* * * * *